(12) United States Patent
Haber et al.

(10) Patent No.: US 12,381,012 B2
(45) Date of Patent: Aug. 5, 2025

(54) CLINICAL PREDICTIVE ANALYTICS SYSTEM

(71) Applicant: BATTELLE MEMORIAL INSTITUTE, Columbus, OH (US)

(72) Inventors: Daniel Haber, Columbus, OH (US); Steven W. Rust, Worthington, OH (US)

(73) Assignee: Battelle Memorial Institute, Columbus, OH (US)

( * ) Notice: Subject to any disclaimer, the term of this patent is extended or adjusted under 35 U.S.C. 154(b) by 733 days.

(21) Appl. No.: 17/157,218

(22) Filed: Jan. 25, 2021

(65) Prior Publication Data

US 2021/0142915 A1    May 13, 2021

Related U.S. Application Data

(63) Continuation of application No. 14/578,396, filed on Dec. 20, 2014, now abandoned, which is a continuation of application No. PCT/US2013/047189, filed on Jun. 21, 2013.

(60) Provisional application No. 61/788,935, filed on Mar. 15, 2013, provisional application No. 61/662,732, filed on Jun. 21, 2012.

(51) Int. Cl.
*G16H 50/50* (2018.01)
*G16H 50/30* (2018.01)

(52) U.S. Cl.
CPC ............. *G16H 50/50* (2018.01); *G16H 50/30* (2018.01)

(58) Field of Classification Search
CPC .............................. G16H 50/50; G16H 50/30
See application file for complete search history.

(56) References Cited

U.S. PATENT DOCUMENTS 8,265,955 B2 *   9/2012   Michelson ............. G16H 50/70
                                                                          705/2

* cited by examiner

*Primary Examiner* — Joshua B Blanchette
(74) *Attorney, Agent, or Firm* — Thomas E. Lees, LLC

(57) ABSTRACT

Predictive models are built for the estimation of adverse health likelihood by identifying candidate model risk variables, constructing a model form for an outcome likelihood model that estimates the likelihood of an adverse outcome type using a group of risk variables selected from the set of candidate model risk variables and by classifying each selected risk variable into either a baseline group or a dynamic group. Additionally, predictive models are built by constructing separate baseline and dynamic outcome likelihood model forms and by fitting the constructed model forms to a training data set to produce final models to be used as scoring functions that compute a baseline outcome likelihood and a dynamic outcome likelihood for patient data that is not represented in the training data set. The predictive models can be used with alerting and attribution algorithms to predict the likelihood of an adverse outcome for individuals receiving care.

20 Claims, 11 Drawing Sheets

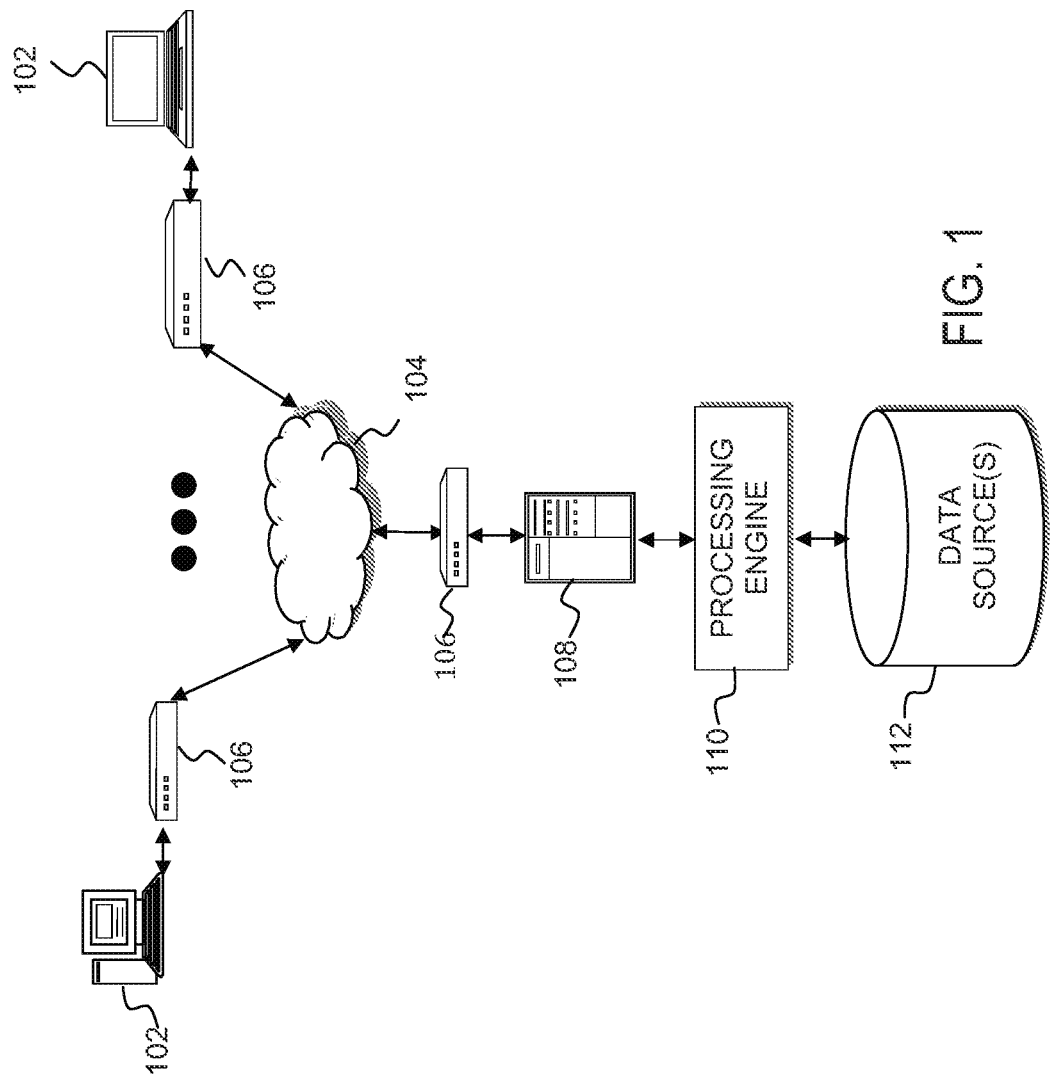

CLINICAL PREDICTIVE ANALYTICS SYSTEM

CROSS-REFERENCE TO RELATED APPLICATIONS

This application is a continuation of U.S. patent application Ser. No. 14/578,396, filed Dec. 20, 2014, entitled "CLINICAL PREDICTIVE ANALYTICS SYSTEM", which is a continuation of International Application No. PCT/US2013/047189, filed Jun. 21, 2013, entitled "CLINICAL PREDICTIVE ANALYTICS SYSTEM", which claims the benefit of U.S. Provisional Patent Application Ser. No. 61/788,935, filed Mar. 15, 2013, entitled "CLINICAL PREDICTIVE ANALYTICS SYSTEM", and U.S. Provisional Patent Application Ser. No. 61/662,732, filed Jun. 21, 2012, entitled "CLINICAL PREDICTIVE ANALYTICS SYSTEM", the disclosures of which are incorporated herein by reference.

BACKGROUND

The present disclosure relates in general to predictive systems for use in the health care industry and in particular, to clinical predictive analytics systems that compute the likelihood of future adverse outcomes for patients receiving medical care, and that identify factors contributing to the adverse outcome likelihood.

Many clinical decisions must be made in the typical course of treating a patient who is undergoing medical care. Often times these decisions affect the overall health and well-being of the patient. Particularly, despite current efforts to apply accepted best practices, it is possible for a patient that receives medical care to suffer from an adverse health outcome, which results from the treatment of, or otherwise occurs after, the original health condition for which the patient received medical treatment. An adverse medical outcome can manifest itself in many forms including for example, an infection acquired during a hospital stay. Further, an adverse outcome may arise in response to, or as a result of, a treatment or procedure. Still further, an adverse outcome may result from an activity during a stay at a hospital, e.g., a patient may slip and fall, etc. The occurrence of adverse health outcomes affects the overall cost of healthcare.

BRIEF SUMMARY

According to aspects of the present disclosure, a computer-implemented process for performing a clinical assessment is provided. The process comprises implementing a data abstraction process that receives as input, electronic patient data about a patient of interest from a first data source, and transforms at least a portion of the received input to standardized format patient data for the patient of interest, which is stored in a second data source. The process also comprises matching the standardized format patient data for the patient of interest to a set of risk variables. The risk variables include at least one variable classified into a baseline group composed of risk variables that are non-modifiable based on provided medical care of a corresponding patient, and at least one variable classified into a dynamic group composed risk variables that are modifiable based on the provided medical care of the corresponding patient. In this regard, the set of risk variables are selected to be predictive of an adverse outcome of interest associated with a physiological condition.

The process still further comprises extracting by a processor, a set of outcome models. Here, the set of outcome models correspond to the adverse outcome type associated with the physiological condition of interest, and include a baseline outcome likelihood model and a dynamic outcome likelihood model. Moreover, the process comprises applying the set of risk variables to the set of outcome models to generate a baseline outcome likelihood and a dynamic outcome likelihood. Also, the process comprises outputting an electronic alert to a remote electronic device to alert a clinician if at least one of the baseline outcome likelihood and dynamic outcome likelihood exceeds a predetermined threshold. The alert provides sufficient information to facilitate an intervention in treating the physiological adverse outcome type associated with the physiological condition of interest by including an attribution associated with at least one risk factor causing the predetermined threshold to be exceeded.

According to further aspects of the present disclosure, a computer-implemented process for triggering an alert responsive to an adverse health likelihood is provided. The process comprises implementing a first data abstraction process that receives as input, electronic patient data about a first patient population, and transforms at least a portion of the received input to standardized format patient data, which is stored as a first training data set. The process also comprises implementing a second data abstraction process that receives as input, electronic patient data about a second patient population, and transforms at least a portion of the received input to standardized format patient data, which is stored as a second training data set.

The process also comprises training an outcome likelihood model form using the first training data set, by an automated computer-implemented selection process, where the outcome likelihood model form evaluates a likelihood of an adverse outcome type associated with a physiological condition of interest. Here, the selection process automatically selects risk variables. The selected risk variables are classified into a baseline group composed of risk variables that are non-modifiable based on provided medical care of a corresponding patient, and a dynamic group composed risk variables that are modifiable based on the provided medical care of the corresponding patient. The process further comprises generating dynamic risk variable model forms from the selected risk variables that predict values for risk variables in the dynamic group as a function of at least one of the risk variables in the baseline group. Still further, the process comprises generating a baseline outcome likelihood model form associated with the adverse outcome type using the outcome likelihood model form and the dynamic risk variable model forms, and generating a dynamic outcome likelihood model form associated with the adverse outcome type using the outcome likelihood model form and at least one of the selected risk variables.

The process yet further comprises fitting the constructed outcome likelihood model form, baseline outcome likelihood model form, and dynamic outcome likelihood model form, to the second training data set comprising electronic patient training data stored in at least one database that includes both outcome data and data values that correspond to the selected risk variables, to produce an outcome likelihood model stored in a first computer memory, a baseline outcome likelihood model stored in a second computer memory, and a dynamic outcome likelihood model stored in a third computer memory.

Yet further, the process comprises collecting by a computer, electronic patient data about an actual patient seeking medical treatment from at least one electronic data source, and automatically applying the electronic patient data to the risk variables in the outcome likelihood model, the baseline outcome likelihood model, and the dynamic outcome likelihood model as scoring functions. The process additionally comprises outputting an electronic alert to a clinician if at least one of the baseline outcome likelihood and dynamic outcome likelihood exceeds a predetermined threshold to facilitate an intervention in treating the physiological condition associated with the adverse outcome type, the electronic alert including an attribution associated with at least one risk factor causing the predetermined threshold to be exceeded.

According to yet further aspects of the present disclosure, a method is provided, for building predictive models for the estimation of adverse health outcome likelihood. The method comprises identifying a set of candidate model risk variables that are associated (e.g., determined to be of interest) to an adverse outcome type. The method also comprises constructing an outcome likelihood model form that estimates the likelihood of the adverse outcome type using risk variables selected from the set of candidate model risk variables. Still further, the method comprises classifying each of the selected risk variables into either a baseline group or a dynamic group. Here, the baseline group is composed of non-modifiable variables (i.e., those selected risk variables that are non-modifiable based on medical care that is provided to a patient). The dynamic group is composed of modifiable variables (i.e., those selected risk variables that are modifiable based on the medical care that is provided to the patient).

Additionally, the method comprises constructing separate baseline and dynamic outcome likelihood model forms associated with the adverse outcome type that estimate the likelihood of the adverse outcome type using the selected model variables. In particular, the method comprises constructing dynamic risk variable model forms that predict values for the selected risk variables in the dynamic group as a function of at least one of the risk variables in the baseline group. The method also comprises constructing a baseline outcome likelihood model form associated with the adverse outcome type using the outcome likelihood model form and the dynamic risk variable model forms. The method still further comprises constructing a dynamic outcome likelihood model form associated with the adverse outcome type using the outcome likelihood model form and at least one of the selected risk variables.

Still further, the method comprises fitting the constructed model forms (e.g., outcome likelihood model form, baseline outcome likelihood model form, and dynamic outcome likelihood model form) to a training data set that includes both outcome data and data values that correspond to the selected risk variables to produce final models (e.g., an outcome likelihood model, a baseline outcome likelihood model, and a dynamic outcome likelihood model), which are used as scoring functions that compute a baseline outcome likelihood and a dynamic outcome likelihood for patient data that is not represented in the training data set.

According to further aspects of the present invention, a method of performing clinical likelihood computations to evaluate patient risk is provided. The method comprises collecting electronic patient data about an actual patient to be monitored for an adverse outcome type. The method also comprises matching the electronic patient data to a set of risk variables for predicting the adverse outcome type. The set of risk variables include at least one variable classified in a baseline group and at least one variable classified in a dynamic group, where the baseline group is composed of non-modifiable variables, and the dynamic group is composed of modifiable variables. The method still further comprises utilizing a scoring algorithm associated with an outcome likelihood model to estimate a baseline outcome likelihood and a dynamic outcome likelihood based upon the electronic patient data matched to the set of risk variables, identifying whether the patient is at-risk based upon the computed baseline outcome likelihood and a dynamic outcome likelihood and providing an alert with attribution if the computed score exceeds a predetermined threshold.

BRIEF DESCRIPTION OF THE SEVERAL VIEWS OF THE DRAWINGS

FIG. 1 is a block diagram of a basic computer system that may be used to implement clinical predictive analytics system components according to aspects of the present disclosure;

DETAILED DESCRIPTION

Figure 2A:
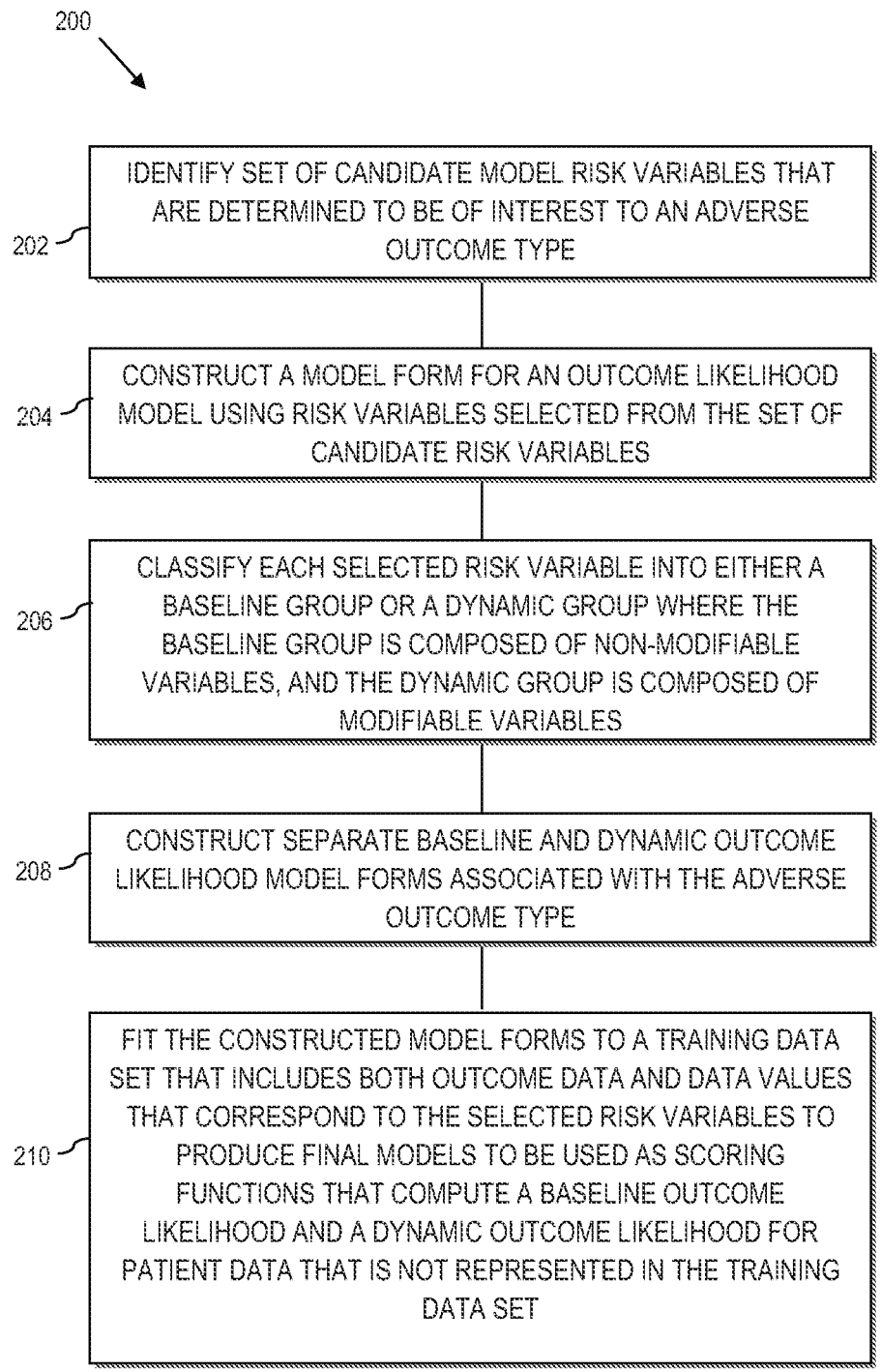
FIG. 2A is a flow chart illustrating a method of building predictive models for the estimation of adverse health outcome likelihood, according to aspects of the present disclosure herein.

According to various aspects of the present disclosure, systems, methods and computer program products are provided that analyze data from various sources and predict the baseline and dynamic likelihoods of an adverse outcome for patients that receive medical attention. Based upon an analysis of available data, clinicians are provided with sufficient contextual information and preventative action decision-making support to facilitate effective intervention.

According to further aspects of the present disclosure, a modeling platform is used to construct an outcome likelihood model and an alerting algorithm. The model and algorithm are utilized to analyze electronic medical patient information and predict a baseline likelihood and a dynamic likelihood that a predetermined adverse health outcome (i.e., a specific event occurring within a specified future time period), will occur. The availability of health risk information may be maximized by imputing missing risk factors. In an example implementation, the model produces a result between 0 and 1, which is compared to a threshold by the alerting algorithm. If the threshold is exceeded, the system provides an alert and identifies risk variables that are associated with patient risk that may be suggestive of mitigation actions.

As an example, a patient is admitted to a hospital with symptoms of a heart attack. During the stay at the hospital, an angiogram is performed to determine whether the patient's coronary arteries are narrowed or blocked. In this test, a liquid dye/contrast agent is injected into the arteries of the patient. The dye is visible on X-ray, to reveal areas of blockage. However, if the patient's kidneys do not properly expel the dye, the patient may suffer kidney failure or damage. Since the patient is in the hospital for a heart attack, the doctors may not be thinking about kidney failure. However, the application of the dye puts the patient at risk of kidney failure. As such, a system set out herein, which is trained to look for the likelihood of kidney failure as its assigned adverse outcome type, can provide alerts to the attending staff if the computed likelihood of kidney failure exceeds a pre-determined threshold. The alert is provided in time to take mitigative action. Moreover, the alert is coupled with attribution data so that the care givers know and understand the reason for the alert. Attribution data attributes risk to variables of the outcome likelihood model.

Platform Overview:

Referring now to the drawings and particularly to FIG. 1, a general diagram of a computer system 100 is illustrated, where components of the computer system 100 can be used to implement elements of a clinical predictive analytic system according to aspects of the present disclosure. The system 100 can be implemented, for instance, within a hospital, clinic or other treatment facility. Alternatively, the system components can be distributed across multiple different locations. Moreover, system components can be implemented by different entities.

The computer system 100 comprises a plurality of processing devices, designated generally by the reference 102 that are linked together by a network 104. As will be described more fully herein, some processing devices 102 of the clinical predictive analytic system 100 are used for model and algorithm development, creation, maintenance, etc., whereas some processing devices 102 are used in a corresponding clinical application, e.g., in a patient's room at a hospital, in a nursing station or in some other location where alerts, such as contextual information and preventative action decision making support, can be acknowledged by treating clinicians.

As a few illustrative examples, the processing devices 102 can include servers, personal computers and portable computers. As used herein, portable computers includes a broad range of processing devices, including notebook computers, tablet computers, smart phones, transactional systems, purpose-driven appliances (e.g., networkable medical machines), special purpose computing devices, personal data assistant (PDA) processors, cellular devices including smart telephones and/or other devices capable of communicating over the network 104.

The network 104 provides communications links between the various processing devices 102, and may be supported by networking components 106 that interconnect the processing devices 102, including for example, routers, hubs, firewalls, network interfaces, wired or wireless communications links and corresponding interconnections, cellular stations and corresponding cellular conversion technologies, e.g., to convert between cellular and tcp/ip, etc. Moreover, the network 104 may comprise connections using one or more intranets, extranets, local area networks (LAN), wide area networks (WAN), wireless networks (WIFI), the Internet, including the World Wide Web, and/or other arrangements for enabling communication between the processing devices 102.

The illustrative system 100 also includes a server 108, which executes at least one processing engine 110 that interacts with at least one corresponding data source 112. The processing engine(s) 110 and data source(s) 112 can support the clinical predictive analysis system and/or other processes, as described in greater detail herein with reference to FIGS. 2A through 8. The results of the processing performed by the server 108 can be communicated to the processing devices 102, e.g., which may be stationed in hospital rooms, at centralized locations, at remote locations, etc.

Figure 2B:
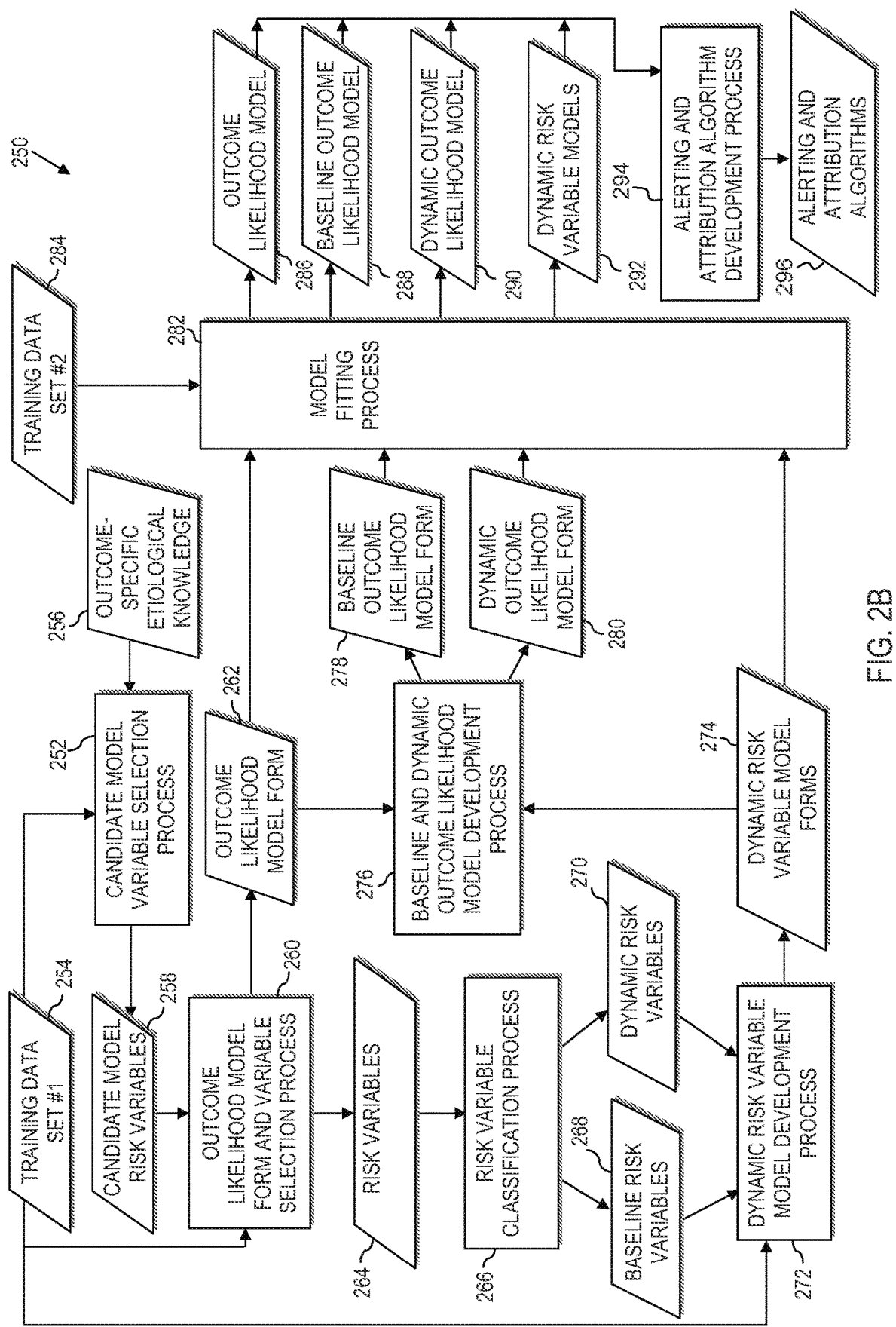
FIG. 2B is a flow diagram illustrating a method for model and algorithm development in a clinical predicative analytic system according to aspects of the present disclosure.

According to illustrative implementations, the overall flow of the clinical predictive analytics system is to first, develop a model to predict at least one predetermined adverse outcome. An example of model development is described in FIGS. 2A and 2B. The models that are built in FIGS. 2A and 2B are applied in a clinical application, an example of which is described in FIGS. 3A and 3B. Moreover, a model that is built using the process set out in FIG. 2A-FIG. 2B may be refined over time. An example approach to refining the model over time will be described herein with reference to FIG. 4.

Notably, the model predicts the likelihood that a given adverse outcome will occur within a prescribed period of time. As such, the system does more than merely predict likelihoods. As a few illustrative examples, a low risk may comprise a risk where the adverse outcome is not likely to occur for a long time. As another example, if the result is a prediction that an outcome is likely to occur, the computation further predicts that the outcome will occur in a defined time frame, e.g., the next 48 hours, 10 days, or other reasonable period of time, given a number of factors, including the adverse outcome type.

The flows, methods, processes, etc., described with reference to any of FIG. 2A through FIG. 8 can be implemented on one or more of the system components of FIG. 1, e.g., the processing engine 110 executing on the server 108. Moreover, the flows, methods, processes, etc., with reference to any of FIG. 2A through FIG. 8 can be implemented as methods or computer program product code that is embodied on a computer readable storage media (e.g., computer readable hardware). The code is executable by a processor to cause the processor to perform the corresponding methods set out herein.

Model Development:

Referring to FIG. 2A, a method 200 of building predictive models for the estimation of adverse health likelihood is illustrated. The method 200 includes numerous steps of a technical character that solve, among other issues, the technical problem of how to build a predictive analytics platform providing a generalized model that predicts the likelihood of an adverse outcome, which weighs or otherwise focuses on/emphasizes those elements of risk that can be managed. This predictive modeling platform can account for individual characteristics, such as a specific elderly person in atypically good health, or a specific otherwise youthful person in unusually poor health by establishing an overall risk of adverse outcome into a baseline outcome likelihood and a dynamic outcome likelihood.

Features that provide an inventive technical contribution include identifying, at 202, a set of candidate model risk variables that are determined to be of interest to an adverse outcome type. The method 200 further includes constructing, at 204, a model form for an outcome likelihood model that estimates the likelihood of the adverse outcome type using a group of risk variables selected from the set of candidate model risk variables during the model development process.

For instance, in particular illustrative example, in the construction of the model form for the outcome likelihood model, the selection of risk variables from the set of candidate risk variables may be implemented by selecting at least one risk variable that has a reconcilable relationship with an etiology of the adverse outcome type. As another example, at least one risk variable may be selected based upon a computed statistical relationship for predicting the adverse outcome type.

The method 200 also includes classifying, at 206, each selected risk variable into either a baseline group or a dynamic group, where the baseline group is composed of non-modifiable variables, and the dynamic group is composed of modifiable variables. In an exemplary implementation of the method, the selected risk variables should include at least one variable classified into the baseline group and at least one variable classified into the dynamic group.

The method 200 further includes constructing, at 208, separate baseline and dynamic outcome likelihood model forms associated with the adverse outcome type that estimate the likelihood of the adverse outcome type using the selected model variables. In practice, the construction at 208 may comprise constructing a model form for each dynamic risk variable, where the constructed model form may be used to estimate the dynamic risk variable as a function of one or more of the baseline risk variables. In this example, the construction at 208 may further comprise constructing a model form for a baseline outcome likelihood model that estimates the likelihood of the adverse outcome type using only baseline risk variables. For instance, in a particular illustrative example, the model form may be constructed by replacing each dynamic risk variable in the outcome likelihood model form with the corresponding model form for estimating the dynamic risk variable as a function of baseline risk variables. A model form for a dynamic outcome likelihood is based upon the outcome likelihood model, the baseline outcome likelihood model, and any predictive models for dynamic variables that are employed in the baseline outcome likelihood model.

Thus conceptually, a model form for an (overall) outcome likelihood, and separate baseline and dynamic outcome likelihood model forms may be implemented by computing an overall outcome likelihood; constructing models that estimate each dynamic model variable as a function of the baseline model variables; computing the baseline outcome likelihood using model variables in the baseline group and using the estimated values of the dynamic model variables; and computing the dynamic outcome likelihood by defining an outcome likelihood model component corresponding to each dynamic risk variable and aggregating across comparisons of the component magnitude when calculated with the actual dynamic risk variable value to the component magnitude when calculated with an estimated value of the dynamic risk variable.

The method 200 still further includes fitting, at 210, the constructed model forms to a training data set that includes both outcome data and data values that correspond to the selected risk variables to produce final models to be used as scoring functions that compute a baseline outcome likelihood and a dynamic outcome likelihood for patient data that is not represented in the training data set.

The method 200 may also optionally include constructing alerting and attribution algorithms that determine when to alert clinical staff and generate an attribution assessment that identifies important risk variables contributing to an adverse outcome likelihood risk by evaluating the contribution of the risk variables with respect to at least one of the baseline outcome likelihood and the dynamic outcome likelihood associated with an occurrence of an adverse outcome and indicating at least one evaluated model variable that is determined to be a key contributor to the overall outcome likelihood.

The method 200 may also optionally comprise mapping actual patient data that is not represented in the training data set to the selected model variables. The method 200 may further comprise fitting the constructed model form to the mapped patient data, performing scoring calculations using the scoring algorithm and outputting a presentation of the results as a prediction of the likelihood of the adverse outcome for the patient represented by the actual patient data.

Model Platform:

Referring to FIG. 2B, a flow diagram illustrates a model development system 250, which outlines an approach for developing models for predictive healthcare, according to aspects of the present disclosure. The model development system 250 can be used, for instance, to implement the method 200 of FIG. 2A. Moreover, the model development system 250 can be implemented on the hardware (or a portion thereof) as described with reference to FIG. 1.

In general, the flow diagram for the model development system 250 defines a generalized health outcome risk characterization device designed to generate models that will allow predictive systems to characterize the risk of a future adverse health outcome for patients that receive medical attention. In an example implementation, estimated outcome likelihoods are computed according to an additive statistical model that is developed from retrospective data associated with a set of training patients.

The model development system 250 may be used to build a particular and unique model for each adverse health outcome of interest. In this regard, the system is flexible to accommodate multiple types of adverse health outcomes. Moreover, the model development can be scaled and/or customized. As such, a facility can uniquely tailor the model to their operations, or a facility such as a hospital can adopt a best practices approach derived from local, regional or national data. Other deployments are also possible, and the particular scale and customization will likely depend upon the particular application.

In general, the model development system 250 can be used to develop models that are applied to an individual patient, or the model development system 250 can be utilized to develop models that are applied retrospectively across a database to examine an entire population of patients. In this manner, the model development system 250 can be utilized to provide information that is indicative of something quantitative about the root causes of the adverse outcome within a population. By understanding the root causes, policy can be altered or examined to determine whether a change in procedure at a health care facility is in order.

An illustrative exemplary implementation trains to an overall likelihood of an adverse outcome based upon baseline and dynamic variables. The implementation takes a "best guess" at dynamic variables (referred to as predicted dynamic variables) based only on baseline variables. Thus, the implementation estimates baseline risk as a function of baseline risk variables and "best guesses" at dynamic risk variables. The implementation then determines a dynamic outcome likelihood as a function of the actual values of the dynamic risk variables compared to the "best guess" values for the dynamic risk variables.

Candidate Model Variable Identification:

A candidate model variable selection process 252 utilizes a first training data set 254 and outcome specific etiological knowledge 256 to identify (and optionally generate) a set of candidate model risk variables 258 that are determined to be of interest to an adverse outcome type. The candidate model variable selection process 252 may be used for instance, to implement the identifying step at 202 in FIG. 2A.

The outcome specific etiological knowledge 256 identifies risk factors, e.g., concepts that characterize factors that are of interest in predicting the likelihood of a particular adverse outcome for which a model is to be trained. In general, the outcome specific etiological knowledge 256 includes information that pertains to outcome specific causal factors that may lead to an associated adverse outcome of interest. The outcome specific etiological knowledge 256 may also include information such as causal relationships among risk factors, conditions, origins, or reasons for an outcome specific condition. In illustrative implementations, the outcome specific etiological knowledge 256 can be derived from domain knowledge, research, literature review, information gathered based upon consultations with healthcare professionals, knowledge of risk factors for which useful information exists in patient records, etc.

The first training data set 254 can come from any suitable location. In an illustrative example, a first database stores electronic patient training data from which the first training data set 254 is extracted. The training data includes data useful in training the system based upon the specific adverse outcome of interest. Moreover, the training data should be representative of the types of data that will be available in a corresponding clinical application.

In an illustrative example, the first training data set 254 includes both outcome data (information pertaining to the adverse outcome that the system is trying to predict/prevent), and non-outcome data, i.e., training data that is not outcome data. In certain environments, the patient training data may be in a proprietary format or some data format that is difficult or undesirable to work with. Accordingly, it may be necessary to convert or otherwise transform the first training data set 254 into a standardized generic data format. According to aspects of the present disclosure, a data abstraction process is optionally utilized to transform base-patient training data, i.e., first training data set 254 in proprietary formats into a standardized generic format. This approach enables, for example, the reuse of key concepts across training data sets, and facilitates consistent processing of the training data.

The candidate model risk variables 258 can involve some algorithmic processing of basic patient data from the first training data set 254. Thus, in general, the identification of candidate model variables 258 is a result of reconciliation of the risk factors identified in outcome specific etiological knowledge 256 and variables (e.g., non-outcome patient training data) that may be calculated, derived, transformed, or otherwise obtained from the first training data set 254.

According to an illustrative implementation, the candidate model variable selection process 252 evaluates the kind of data that is available in the first training data set 254, e.g., the non-outcome training data, in view of the risk factors identified in the outcome specific etiological knowledge 256. In yet further illustrative examples, formulas are constructed based upon identified risk variables, where the candidate model variables can be used as indicators of the risk factors identified in the outcome specific etiological knowledge 256.

In illustrative exemplary implementations, candidate model risk variables 258 are identified for as many risk factors as possible. In illustrative implementations, the system is configured to err on the side of inclusion. Also, candidate model risk variables developed for one adverse outcome type may be reusable for other outcome types, depending upon the application.

In certain illustrative embodiments, candidate model risk variables can be organized around any desired system. For instance, it may be desirable to organize candidate model risk variables around body systems, e.g., cardiovascular, respiratory, etc., molecular pathways, or other classification system.

Outcome Likelihood Model Development:

An outcome likelihood model form and variable selection process 260 receives as inputs, data from the first training data set 254 and the candidate model risk variables 258 to generate an outcome likelihood model form 262 and a list of risk variables 264 employed in the model form 262. The candidate model risk variables 258 are derived or otherwise obtained at least partially based upon outcome specific etiological knowledge 256. As such, the candidate model risk variables 258 reflect comorbidity effects within the outcome likelihood model. The outcome likelihood model form and variable selection process 260 may be used for instance, to implement the constructing step at 204 in FIG. 2A.

For a given training patient set, the outcome likelihood model form 262 (i.e., statistical model) can include demographic and clinical variables as independent variables and a binary indicator of outcome as a dependent variable. Moreover, the element of time can be accounted for in numerous ways. As noted above, the element of time is predicted at some finite future that preferably provides sufficient time for mitigative action to be taken. For instance, time can be factored into the dynamic risk variables themselves. Moreover, time can be accounted for in other model parameters. Here, the time is any reasonable finite time, e.g., 48 hours, the length of a hospital stay, a measure of hours, days, or other reasonable measure in view of the adverse outcome of interest.

Various aspects of the present disclosure characterize data in two general categories, including baseline data and dynamic data. Baseline data comprises a record for which the data value is deemed to be non-modifiable based on the medical care that is provided to the patient. Baseline data thus represents a data value that will not change (from its current state), or a record where the data value is not expected to change from its current state over a time period of interest. For instance, a time period corresponding to the duration of the patient's hospital visit can be used to identify a baseline variable. Of course, other reasonable time frames and reference time points may be used for a given adverse outcome being modeled. In addition, a data value that changes over time but in a manner that can be unrelated to the medical care that is provided to the patient can also be identified as a baseline variable.

Correspondingly, dynamic data includes a record for which a data value changes, can change, or is expected to change over the time period of interest where the change can be related to the patient's condition and/or medical care that is provided to the patient.

As a few illustrative examples, baseline data can include the date that a patient is admitted into a hospital. Baseline data can also include patient data as of a date of admission into a hospital, e.g., the patient's weight, height, age, etc., at the time of being admitted. Correspondingly, dynamic data may comprise blood pressure, heart rate or other vitals, etc., that can change over time in a manner that can be related to the medical care that is provided to the patient and the condition of the patient.

Correspondingly, risk is divided into baseline risk and dynamic risk. This approach provides the clinician with an opportunity to manage dynamic risk to lower the probability of an adverse health outcome. More particularly, baseline risk is risk that is not affected by patient care (more limited opportunity to mitigate risk) e.g., the baseline likelihood is based upon static patient data that is available at the time of admission. This is risk that is inherent to the patient. As an example, certain patients may pose risks that are particular to the person due to past medical history and current symptoms.

Correspondingly, dynamic risk is affected by care received in the hospital and can change due, for example, to changes in conditions of the patient while in the hospital. Thus, dynamic risk is risk that is affected by the medical care that the patient receives while in the hospital as reflected in the patient's condition which is characterized by dynamic patient data that is updated with some frequency during the patient's hospital stay.

The outcome likelihood model form and variable selection process 260 is guided by the first training data set 254 (which includes non-outcome as well as outcome data). In this regard, the known outcome data from the first training data set 254 can be used to judge the model being developed.

In an illustrative example, the outcome likelihood model form and variable selection process 260 outputs a model that takes the general form: $Y=\log(P/(1-P))=\beta_0+\beta_1 x_1+ \ldots +\beta_k x_k$. In this example implementation, estimated outcome likelihoods are computed based upon logistic regression models, thus predicting the likelihood that a person will experience an adverse health outcome in the near future, e.g., next 48 hours. This approach involves a down-selection of candidate model risk variables 258 based on clinical judgment, predictive power and statistical significance in order to select the risk variables 264.

As an example, an outcome likelihood model may be expressed as $\beta_1 x_1+ \ldots +\beta_k x_k$. In this example, there are k risk variables where $\beta_1$-$\beta_k$ represent model coefficients. In practice, the first training data set 254 is used to fit the model. The model then determines if $\beta$ should be adjusted up or down, whether factor $x_i$ should be dropped, etc. The model itself determines which parameters are important to allow the system to predict adverse health outcomes.

A risk variable classification process 266 classifies each risk variable involved in the outcome likelihood model form into either a baseline group or a dynamic group, where the baseline group is composed of non-modifiable variables, and the dynamic group is composed of modifiable variables, in a manner analogous to the other examples for "baseline" and "dynamic" as described more fully herein. The risk variable classification process 266 may be used to implement the classifying step at 206 in FIG. 2A.

For instance, as illustrated, the risk variable classification process 266 divides the risk variables 264 by dividing them into baseline risk variables 268 and dynamic risk variables 270. Variables deemed to be non-modifiable based on the medical care that is provided to the patient are classified as baseline risk variables 268 (also referred to generally as baseline variables). Correspondingly, variables affected by the medical care that the patient receives while in the hospital will be classified as dynamic risk variables 270 (also referred to generally as dynamic variables).

A dynamic risk variable model development process 272 takes as inputs, the baseline risk variables, the first training data set 254, and the dynamic risk variables 270. The dynamic risk variable model development process 272 outputs dynamic risk variable model forms 274 that may be employed to predict dynamic risk variables 270 as a function of baseline risk variables 268. The dynamic risk variable model development process 272 may employ all the data in the first training data set 254, or only a subset of the data in the first training data set 254, such as a subset of data corresponding to patients that do not experience one or more of the adverse health outcomes of interest.

A baseline and dynamic outcome likelihood model development process 276 takes as input the outcome likelihood model form 262 and the dynamic risk variable model forms 274 and outputs a baseline outcome likelihood model form 278 and a dynamic outcome likelihood model form 280. The baseline and dynamic outcome likelihood model development process 276 can thus be used to implement the constructing step 208 of FIG. 2A.

In the illustrated implementation, the baseline outcome likelihood model form 278 is created by substituting dynamic risk variable model forms 274 for dynamic risk variables wherever dynamic risk variables appear within the outcome likelihood model form 262. The dynamic outcome likelihood model form 280 is created by defining an outcome likelihood model component, a component of the outcome likelihood model form 262, corresponding to each dynamic risk variable and comparing the component magnitude when calculated with an actual dynamic risk variable value to the component magnitude when calculated with an estimated value of the dynamic risk variable produced by a dynamic risk variable model form.

Correspondingly, the dynamic outcome likelihood model form 280 can be based on a set of dynamic risk variable scores, one for each risk variable, where a score is calculated as the magnitude of the corresponding outcome likelihood model component calculated with an actual dynamic risk variable value minus the magnitude of the same outcome likelihood model component calculated with estimated values of the predictor variable produced by a dynamic risk variable model form 274.

In one embodiment, the dynamic outcome likelihood model form 280 is the outcome likelihood model form 262 minus the baseline outcome likelihood model form 278. In another embodiment, the dynamic outcome likelihood model form 280 is the sum over a set of dynamic risk variable scores. In yet another embodiment, the dynamic outcome likelihood model form 280 is the sum over a set of dynamic risk variable scores which are greater than zero. For instance, in certain examples, a computed overall likelihood may be less than a baseline likelihood. By way of illustration, an older person is expected to have higher blood pressure than a relatively younger person. However, if a particular older patient has unusually low blood pressure due to good health, the dynamic likelihood may be negative or the overall likelihood of an adverse outcome (where blood pressure is a dynamic variable) may be less than the baseline likelihood.

The outcome likelihood model form 262, dynamic risk variable model forms 274, baseline outcome likelihood model form 278, and dynamic outcome likelihood model form 280 all contain statistical parameters that are estimated by fitting the constructed model forms to a training data set that includes both outcome data and data values corresponding to the selected risk variables involved in the model form to derive models that can be used as scoring algorithms to estimate a baseline outcome likelihood and a dynamic outcome likelihood for patient data that is not represented in the training data set.

More particularly, a model fitting process 282 fits the model forms (outcome likelihood model form 262, dynamic risk variable model forms 274, baseline outcome likelihood model form 278, and dynamic outcome likelihood model form 280) to a second training data set 284 to estimate the statistical parameters associated with each model and outputs an outcome likelihood model 286, baseline outcome likelihood model 288, dynamic outcome likelihood model 290, and dynamic risk variable models 292. The model fitting process 282 may be used to implement the fitting step at 210 of FIG. 2A.

The second training data set 284 may be the same as the first training data set 254, partially unrelated to the first training data set 254, or completely unrelated to the first training data set 254.

Alerting and Attribution Algorithm:

The model development system 250 may also optionally include an alerting and attribution algorithm development process 294. As illustrated, the alerting and attribution algorithm development process 294 receives as inputs, the outcome likelihood model 286, baseline outcome likelihood model 288, dynamic outcome likelihood model 290, dynamic risk variable models 292, or any combination thereof, and outputs alerting and attribution algorithms 296.

For instance, in an illustrative implementation, the alerting and attribution algorithm development process 294 optionally generates an alerting algorithm that compares computed values for at least one of the overall outcome likelihood, baseline outcome likelihood, and dynamic outcome likelihood against a predetermined thresholds, where the alerting algorithm thresholds are based upon a balancing of true positive and false positive behavior.

However, in an alternative illustrative implementation, an alerting and attribution algorithm development process 294 receives as inputs, the baseline risk variables 268, dynamic risk variables, 270, the baseline outcome likelihood model 288, dynamic outcome likelihood model 290 and the second training data set 284 (e.g., outcome and non-outcome data) to output one or more alerting and attribution algorithms 296. In illustrative implementations, the alerts generated by the alerting and attribution algorithm development process 294 are generated based upon a comparison of dynamic and baseline risk in view of available patient data, and are characterized in terms of sensitivity and specificity, which are embodied in a fixed-threshold alert value. In an example implementation, the user can select an alerting threshold that balances the competing goals of minimizing false negatives and false positives. Receiver-operator characteristic curves are used to characterize true positive/false positive behavior for all possible thresholds and to aid in threshold selection.

For instance, the formula variables (values), including predicted outcome data $\hat{Y}_0 \ldots \hat{Y}_n$ and actual outcomes can be used to set the threshold.

Attribution:

As noted in greater detail herein, an alert provides information to a clinical staff in response to the system detecting that a potentially preventable adverse outcome is likely to occur in the future. Thus, "time to risk" is a factor that may be accounted for in the model development process. For instance, the outcome may be predicted in some finite time, e.g., 48 hours from a particular event, at some time during the patient hospital stay, etc. As such, the processing is more sophisticated than mere aggregation.

Attribution data builds additional information into an alert by providing information about what is likely to be causing the alert to be triggered. In an illustrative implementation, the attribution data relates risk to causal factors to facilitate identification of actions to mitigate risk. Thus, an alert may indicate the high likelihood of the adverse outcome is due to factors X, Y, Z. The alert may further indicate that the adverse outcome may be mitigated by taking the course of action involving steps A, B and C.

The alerts are distinguished by determining when to alert and how to attribute an outcome. For instance, assume that $\hat{Y}_0 \ldots \hat{Y}_n$ is the predicted outcome between 0-1, i.e., the likelihood that the outcome will occur. When an alert is to be given, the system applies attribution to tell what percent of risk is coming from each risk variable. For example, assume that a value of 0.9 is computed and that the value 0.9 exceeds the established threshold. The system goes back to the outcome likelihood model, e.g., $y=\beta_0+\beta_1 x_1+ \ldots +\beta_k x_k$ and looks at the contribution of one or more variables. In an illustrative example, contribution of the $i^{th}$ factor is computed as: $\beta_i x_i/(\hat{Y}-\beta_0) \times 100$.

As further illustrative examples, the system can utilize any number of rules, e.g., to zero out negatives or utilize other desired procedures to determine the contributions of individual risk variables.

Missing Data Imputation:

Imputation of missing risk variable values is useful for instance, in applications where the alerting and attribution algorithm development process 294 utilizes a scoring function in developing an alerting algorithm. If there is no value for a given risk variable, then the system may not be able to calculate a score. As such, imputation is utilized to put a "best guess" value in the model. For instance, assume that a model is considered, which utilizes 10 factors $X_1 \ldots X_{10}$ but $X_3$ is missing. Using missing data imputation, as set out herein, the process computes a predicted value for $X_3$ based upon other variables that are available to the process and which are known to correlate to the missing factor. By way of example, the process can impute a missing value by substituting a predictor based only upon a correlation of available factors that fit the model. Thus, for instance, the system can predict $X_3$ using $X_1$, $X_5$ and $X_{10}$, where $X_1$, $X_5$ and $X_{10}$ have known values and correlate to $X_3$. The system may also take advantage of modeling approaches to deal with missing data.

Contribution Associated with Risk Factor:

According to illustrative aspects of the present disclosure, the alerting and attribution algorithm development process 294 evaluates the contribution of the dynamic risk variables by producing a vector of indices characterizing the strength of the contributions of individual dynamic risk variables to the dynamic outcome likelihood. The vector of indices may be produced such that the percentage contribution for all evaluated dynamic risk variables is 100 percent.

A statistical model, including the estimated model coefficients, is used by the system to produce "percent contribution" vectors for new patients in a clinical application, an example of which is described with reference to FIG. 3B. For a given health outcome, the percent contribution associated with a specified risk factor is determined by comparing the components of the statistical model that involve the specified risk factor to the components that do not involve the specified risk factor. In illustrative implementations, a vector of risk contributions is defined where the risk contributions sum to 100%.

Correspondingly, the alerting and attribution algorithm development process 294 evaluates the contribution of the baseline risk variables by producing a vector of indices characterizing the strength of the contributions of individual baseline risk variables to the baseline outcome likelihood.

Collective Adverse Outcome Type

According to an illustrative aspect of the present disclosure, a collective adverse outcome type may be defined to have occurred if one or more of a first adverse outcome type and a second adverse outcome type (or any number of outcome types for that matter) occurs. In this regard, the collective adverse outcome type may be used to predict the patient risk associated with a collection of individual adverse outcome types. The model development system 250 may be applied to a collective adverse outcome type. In this case, candidate model variables are identified, that are determined to be of interest to at least one of the first adverse outcome type and the second adverse outcome type. Moreover, risk variables are selected from the candidate model variables by selecting model risk variables for predicting the first adverse outcome type and selecting model risk variables for predicting the second adverse outcome type. In this exemplary implementation, an attribution assessment may be generated that identifies important risk variables for the collective adverse outcome type.

The attribution assessment is generated by evaluating the contribution of the risk variables with respect to at least one of the baseline outcome likelihood and the dynamic outcome likelihood associated with an occurrence of the first adverse outcome type, the second adverse outcome type or both and indicating at least one risk variable that is determined to be a key contributor to an outcome likelihood of the collective adverse outcome type. For instance, evaluating the contribution of the risk variables comprises producing a vector of indices characterizing the strength of the contributions of individual risk variables to an outcome likelihood of the collective adverse outcome type. Moreover, generating an attribution assessment may further include identifying at least one individual adverse outcome type that is a key contributor to the collective overall outcome likelihood and may further include producing a vector of indices characterizing the strength of the contributions of individual adverse outcome types to an outcome likelihood of the collective adverse outcome type. The vector of indices may be produced such that the percentage contribution for all individual outcome types involved in defining the collective outcome type is 100 percent.

Multiple Etiological Model Integration:

According to yet further aspects of the present disclosure, attribution information is provided based upon an analysis of multiple adverse event outcomes. Attribution across multiple adverse outcomes can provide information such as: a likelihood of any adverse outcome, attribution of the likelihood to different types of adverse outcomes, and the attribution of risk factors for the likelihood of any adverse event. The analysis of multiple adverse event outcomes can be implemented by utilizing outcome-specific etiological knowledge for multiple individual adverse outcome types that can interact (i.e. cardiac and kidney failure models).

Knowledgebase:

The method 200 of FIG. 2A and the corresponding model development system 250 of FIG. 2B may further include the incorporation of a knowledgebase. That is, the outcome specific etiological knowledge 256 employed in the candidate model variable selection process 252 may be obtained by accessing a knowledgebase that includes such etiological knowledge for one or more adverse outcome types.

For instance, a method of identifying a set of candidate model risk variables at 202 of FIG. 2A may be implemented by identifying a specific physiological condition of interest associated with the adverse outcome type and obtaining diagnostic information based upon the identified specific physiological condition. The method may further include obtaining clinical intervention information for interventions that are likely to be appropriate interventions for the physiological condition of interest, populating a knowledgebase with information that relates the obtained diagnostic information to the physiological condition of interest and that relates the obtained clinical intervention information to the physiological condition of interest. Still further, the method comprises selecting the set of candidate model variables using knowledge extracted from the populated knowledgebase.

The method may also include identifying other physiological conditions that are related to the physiological condition of interest. Correspondingly, the knowledgebase may be populated by information that relates these other identified physical conditions to the physiological condition of interest.

In this exemplary implementation, diagnostic information may be obtained by identifying diagnostic criteria employed to diagnose the physiological condition, identifying other physical conditions that contribute to the physiological condition of interest, identifying corresponding risk metrics of the identified diagnostic criteria, identifying electronic medical record (and other) data fields necessary to employ the diagnostic criteria, or any combination thereof. Likewise, clinical intervention information may be obtained by identifying at least one of medical procedures and therapeutic substances employed to treat the specific physiological condition of interest and identifying at least one of medical procedures and therapeutic substances employed to treat other physiological conditions that also have an effect on the risk/severity of the physiological condition of interest. In an illustrative application, the model development system 250 may further utilize an ontology of triple types allowed by the knowledgebase to identify queries to elicit the diagnostic information and clinical intervention information to build the knowledgebase. The building of the knowledgebase is described in greater detail herein with reference to FIG. 5 through FIG. 8.

Figure 3A:
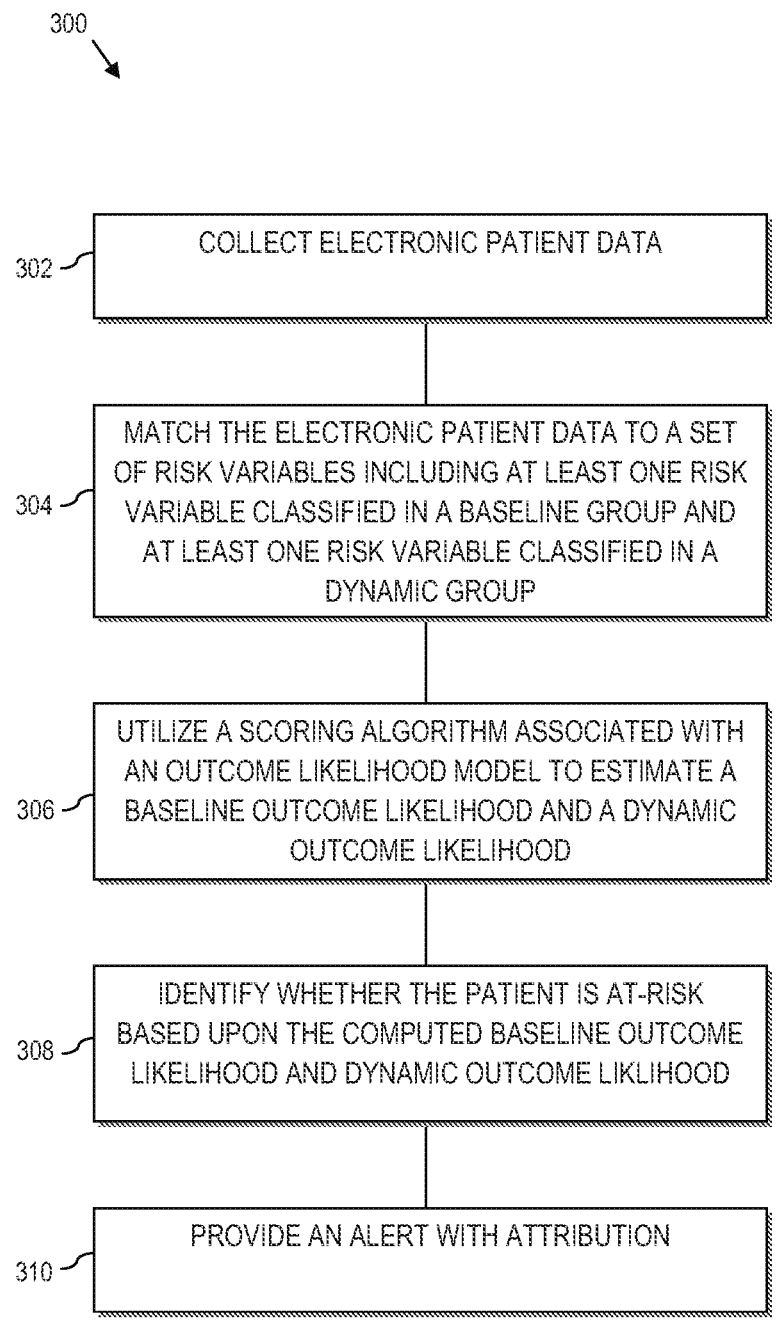
FIG. 3A is a flow chart illustrating a method of performing clinical likelihood computations to evaluate patient risk, according to aspects of the present disclosure.

Clinical Application:

Referring to FIG. 3A, a method 300 of performing clinical likelihood computations to evaluate patient risk is illustrated. The method 300 includes numerous steps of a technical character that solve, among other issues, the technical problem of how to alert a health provider of a likelihood of an adverse outcome in a manner that provides attribution of the risk factors associated with the prediction.

Features that provide an inventive technical contribution include collecting at 302, electronic patient data about an actual patient to be monitored for an adverse outcome type. The method 300 also includes matching at 304, the electronic patient data to a set of risk variables for predicting the adverse outcome type. Here, the selected risk variables include at least one variable classified in a baseline group and at least one variable classified in a dynamic group. The baseline group is composed of non-modifiable variables, and the dynamic group is composed of modifiable variables, as described more fully herein. The method further includes utilizing at 306, a scoring algorithm associated with an outcome likelihood model to estimate a baseline outcome likelihood and a dynamic outcome likelihood based upon the electronic patient data matched to the set of risk variables. Still further, the method includes identifying at 308, whether the patient is at-risk based upon the computed baseline and dynamic outcome likelihoods and providing at 310, an alert with attribution if at least one of the likelihoods exceeds a predetermined threshold.

The method 300 may also comprise collecting the electronic data in a proprietary format and mapping the collected data into a standardized format using a data abstraction process in a manner analogous to that described with reference to FIG. 2B. Also, the method 300 may also comprise imputing a missing model variable based upon other model variables with known values, where the other model variables correlate with the missing model variable. Still further, the method 300 may comprise performing retrospective risk attribution for a population of patients by performing computations to produce risk attribution vectors that apply to groups of patients rather than single patients, utilizing the attribution vectors to draw conclusions across the population as to the likely root cause(s) that lead to eventual adverse outcomes in the patient data, and utilizing the identified root causes to facilitate clinical policy decisions designed to reduce the incidence rate for adverse patient outcomes.

Figure 3B:
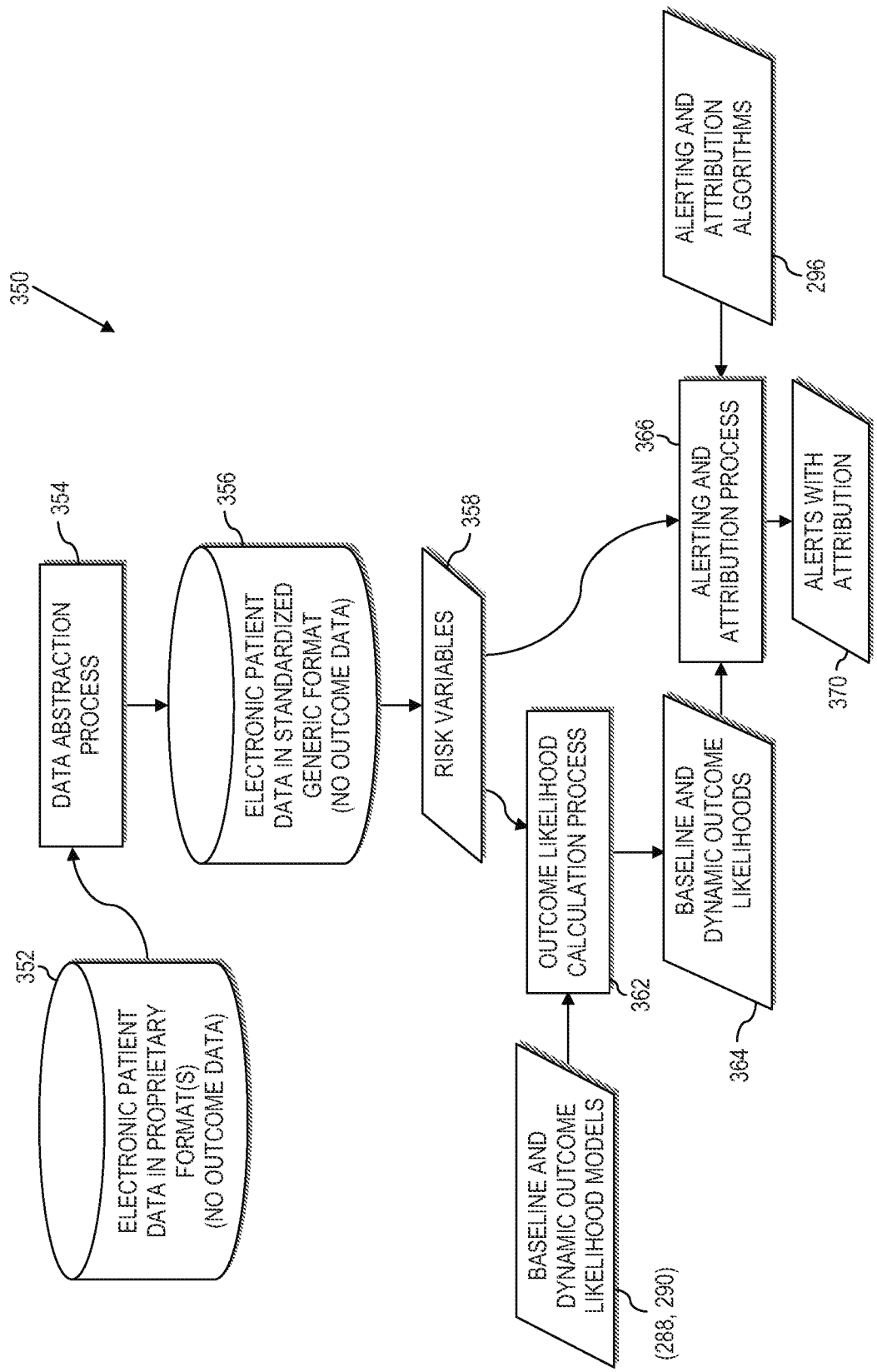
FIG. 3B is a flow diagram illustrating a method of using models and algorithms in a clinical predictive analytic system, according to aspects of the present disclosure.

Referring to FIG. 3B, a clinical application 350 is provided, which is capable of implementing the method 300 of FIG. 3A. The clinical application 350 utilizes the models of FIG. 2A, e.g., one or more of the outcome likelihood model 286, the baseline outcome likelihood model 288, the dynamic outcome likelihood model 290 and the dynamic risk variable models 292 and the alerting and attribution algorithm(s) 296 from FIG. 2B to implement clinical likelihood computations. In this regard, the overall system can be conceptualized as collecting patient data, mapping select data to variables, performing imputation based upon the mapped data if necessary, performing likelihood model/risk factor calculations on the mapped/imputed data, scoring the calculations and outputting a presentation of the results.

Data sources feed the clinical predictive analytics inputs. For instance, as illustrated in this simplified example, electronic patient data is collected. In FIG. 3B, this is represented by data that has been collected into a database 352, which includes electronic patient data in proprietary format. The database 352 of FIG. 3B differs from the database(s) of FIG. 2B in several respects. Notably, patient data in the database 352 relates to data pertaining to an actual patient to be monitored for an adverse outcome, as distinguished from the training patient data used in the model development of FIG. 2B. Moreover, since the databases of FIG. 2B store training data, outcome data is available. Comparatively, in the clinical application 350 of FIG. 3B, the system is in use monitoring actual patient data, so the patient outcome is what the clinical application 350 predicts. The electronic patient data may include information such as demographic data, clinical data, patient medical historical data, physician practice information, ambulance/emergency care information, laboratory results, triage results, nurse measured real time vitals, electronic health records, physiological models, patient medical history, etc.

A data abstraction process 354 receives as input, the electronic patient data in proprietary format(s) and converts, transforms, etc., (i.e., maps) the proprietary data to a standardized generic format that is stored in a fourth database 356. Notably, the data abstraction process 354 can operate in a manner analogous to the data abstraction process of FIG. 2B. Moreover, the conversion of patient data to a standardized format is optional and may not be necessary, e.g., where the patient data is already available in a data format suitable for processing.

By way of example, the data abstraction process 354 can map proprietary medical center data to standardized or generic formats, map proprietary medical data into data types that characterize medical history, observations, labs, orders, medications, outcomes, discharge/disposition, etc. The data abstraction process 354 enables the reuse of key concepts across medical centers. The data collection described above, including the optional data abstraction, may be used to implement the collecting electronic patient data step at 302 of FIG. 3A.

Risk variables 358 are extracted from, computed from or otherwise derived from (i.e., mapped from) the electronic patient data 356. The risk variables 358 of the clinical application may comprise data that is analogous to or otherwise fits the schema of the selected model variables (i.e., the risk variables 264) of FIG. 2B. The risk variable extraction here may be utilized to implement the matching step at 304 of FIG. 3A. Missing data values for necessary variables are imputed in a manner analogous to that set out in the discussion of FIG. 2B.

According to illustrative implementations, dynamic risk is continuously updated as new risk variable data becomes available for a given patient. Moreover, some risk factors can be temporally defined. The risk variables are evaluated against the previously modeled outcome likelihood model. The output risk variables 358 also feed a scoring algorithm and the output of the scoring algorithm feeds into a presentation algorithm that presents a threshold alert and defines the contributing factors for the adverse health prediction. The presentation algorithm thus identifies at-risk patients in time to take mitigative action. Moreover, informed decision support is provided by identifying risk factors for at-risk patients to assist medical staff in identifying mitigative actions and by informing clinical staff about the driving factors behind the computed risk, thus improving patient care.

Baseline & Dynamic Outcome Likelihoods:

More particularly, in the illustrative example, an outcome likelihood calculation process 362 receives as inputs, the baseline outcome likelihood model 288 and the dynamic outcome likelihood model 290 computed by the system of FIG. 2B, and the risk variables 358 extracted from electronic patient data from the database 356, thus representing data about a particular patient receiving medical care. The outcome likelihood calculation process 362 outputs baseline and dynamic outcome likelihoods 364 for the particular adverse outcome of interest. The outcome likelihood calculation process 362 may be utilized to implement the step of utilizing a scoring algorithm associated with an outcome likelihood model to estimate a baseline outcome likelihood and a dynamic outcome likelihood based upon the electronic patient data matched to the set of risk variables at 306 of FIG. 3A.

Alerts:

An alerting and attribution process 366 receives as inputs, the risk variables 358, the baseline and dynamic outcome likelihoods 364 as well as the alerting and attribution algorithms 296 (from FIG. 2B). The alerting and attribution process 366 provides system outputs as alerts with attribution 370. For instance, an output may be an estimated likelihood of adverse outcome (0-100%), aka Estimated Outcome Likelihood. The alerting and attribution process 366 may be utilized to implement the identifying step at 308 and the providing an alert step at 310, respectively, of FIG. 3A.

During runtime of patient monitoring, the system applies statistical models to electronic health record data from the electronic patient data at 352, which is mapped by the data abstraction process 354 to a standardized generic format at 356. The system derives risk variables from the patient data and uses the adverse event-focused predictive models (baseline and dynamic outcome likelihood models) to give clinicians near real-time, patient-specific risk and contextual information via the alerts with attribution at 370.

According to aspects of the present disclosure, the system can decompose the utilized formulas to identify risk factors having the highest contributions to risk. Risk attribution is accomplished for a set of factors by creating a vector of risk contributions that can, for example, sum to 100%. By way of example, for a given health outcome, the percent contribution associated with a specified risk factor is determined by comparing the components of the statistical model that involve the specified risk factor to the components that do not involve the specified risk factor. Information is conveyed to the user of the device via a graphic user interface (GUI) via tabular and graphical displays or by using other suitable approaches.

According to aspects of the present disclosure, the alert indicator is a binary value that is determined by comparing at least one of the baseline and dynamic outcome likelihoods to corresponding threshold values and setting the indicator to 0 if the estimated adverse health outcome likelihood is less than the threshold value and equal to 1 if the estimated adverse health outcome likelihood is greater than or equal to the threshold value. The threshold values associated with the alert indicator are selected to achieve desired values of sensitivity and specificity for the corresponding health outcomes when applied to the data associated with the training patients. This may be used to implement identifying whether the patient is at-risk based upon the computed score at step 310 of FIG. 3A.

According to illustrative aspects of the present disclosure, receiver-operator characteristic curves are used to characterize true positive/false positive behavior for all possible thresholds. This can be useful, for instance, to aid in threshold selection. The performance of fixed threshold alerting procedures is characterized in an illustrative example, by plotting sensitivity (e.g., normalized to a range of 0-1) vs. (1-specificity) (e.g., also normalized to a range of 0-1). If the area under the curve is 1, then optimal results are obtained. The user can tune the optimal point along the curve for a given application based upon a number of factors.

When computing the attribution of outcome risk to contributing factors, the data is conceptually organized in the form of a percent contribution vector. Each element of the percent contribution vector contains the percent contribution to the outcome risk associated with a specific risk variable. The attribution of adverse health outcome risk may be applied to groups of risk factors by summing the percent contributions of the individual risk factors in each group. This may be utilized to implement the providing an alert with attribution step at 312 of FIG. 3A.

According to aspects of the present disclosure, alerts can be tailored/customized. By way of illustration, and not by way of limitation, alerts can be provided for different severity levels and for routing to specific provider roles. Thus, an alert can be customized to address a need for urgent action, such as when kidney failure is imminent. Comparatively, a different alert may be utilized when an action is required at a non-imminent future time, e.g., 24 hours out. Moreover, an alert intended for a doctor can be different from an alert intended for a nurse. Other alert customizations are possible within the present disclosure.

Root Cause Analysis:

According to still further aspects of the present disclosure, retrospective systemic root cause analysis is utilized to support clinical policy decision making. Basically, the root cause analysis uses retrospection of a population of data to draw conclusions across the population as to the likely root cause(s) that lead to the eventual adverse outcomes identified within the patient data. As an example, contribution vectors are produced across a plurality of patients. The contribution vectors capture various potential root causes, symptoms and the ultimate outcomes across the patient data of a plurality of patients for a given adverse health outcome.

Instead of analyzing the contribution vectors at the point of care for a given patient, the system analyzes the contribution vectors across patients to assess systemic root causes. The contribution vectors, when combined with known outcomes for the patients, are used to inform the system as to the reasons that specific adverse event patterns are occurring. As such, clinical policy decisions can be made, to respond to detected patterns.

Figure 4:
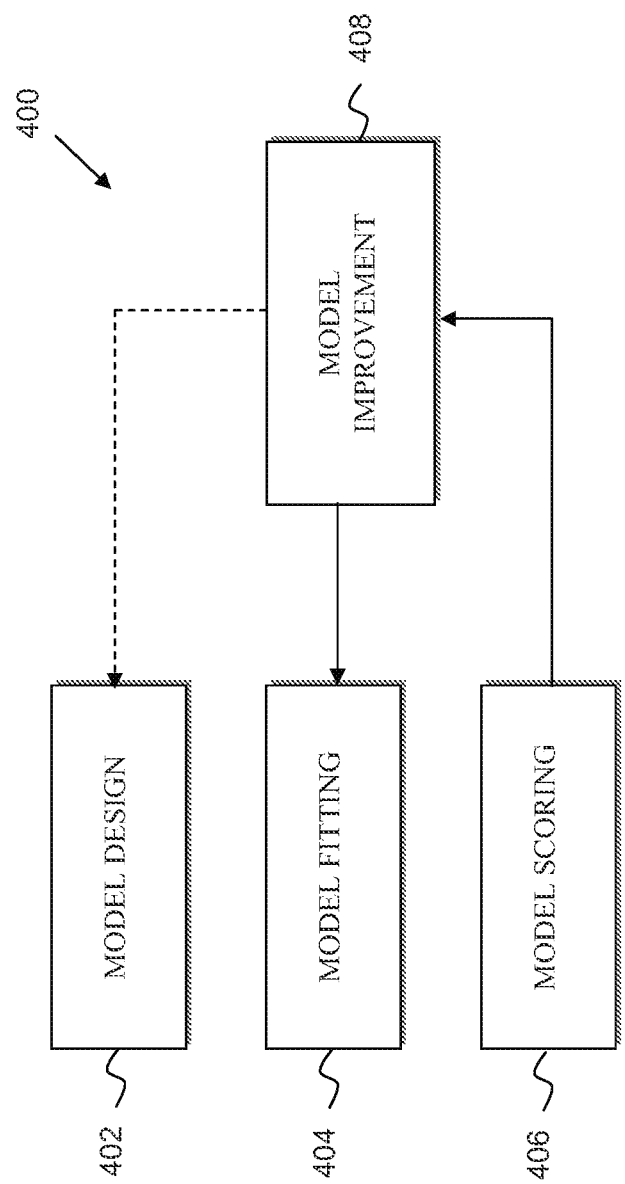
FIG. 4 is a block diagram of a feedback loop that is utilized to analyze the developed models for model changes according to aspects of the present disclosure.

Model Refinement:

Referring to FIG. 4, a block diagram illustrates a feedback loop 400 that facilitates modification of the developed models. For instance, the feedback loop 400 could be used for continual improvement, periodic improvement or improvement at other desired intervals. As an illustrative example, a model design process 402 is utilized to design an operational model for an adverse health outcome of interest. A model fitting process 404 is utilized to fit patient data to the designed model. The model design 402 and model fitting 404 can be implemented, for instance, by the process described above with reference to FIG. 2.

A model scoring process 406 scores the model design at 402 and the model fitting at 404. As an example, during clinical application of the present disclosure (FIG. 3), data may be collected to include risk variables and alerting/attribution data. This data may further be augmented with known outcome data for the patients that were monitored. This augmented data can be used to score the likelihood, alerting and attribution models employed. The scoring results are fed into a model improvement process 408 that can then be used to modify the model design at 402, the model fitting at 404 or combinations thereof.

The feedback loop 400 can be utilized to help assess whether mitigative action was taken that was consistent with the contributing factor identification and whether the adverse event actually manifested. This operational information is useful, for instance, in assessing the quality of the system in an operational context and for recalibrating the models and software for operation.

Clinical Knowledgebase:

Given a physiological condition of interest, at least three general inquiries can be explored. How is the physiological condition of interest diagnosed? Are there candidate interventions to address the physiological condition? Are there any related physiologies? According to aspects of the present disclosure herein, these questions are addressed in a logically organized manner that results in the creation of a clinical knowledgebase that finds numerous uses within the context of the clinical predictive analytics system described more fully herein. For instance, the knowledgebase can be used to build some or all of the outcome specific etiological knowledge used to select candidate model risk variables related to the causal factors associated with an adverse outcome of interest, as described with reference to FIG. 2B.

Building A Clinical Knowledgebase:

According to aspects of the present disclosure, a method and system are provided, for building a multi-conditional model framework that is useful for identifying risk factors related to a physiological condition of interest. More particularly, the model is useful to serve as a framework for building a knowledgebase as will be described in greater detail herein. For instance, these methods and systems may be used to produce a knowledgebase (described with reference to FIG. 7) that can provide the outcome specific etiological knowledge 256 of FIG. 2B.

Figure 5:
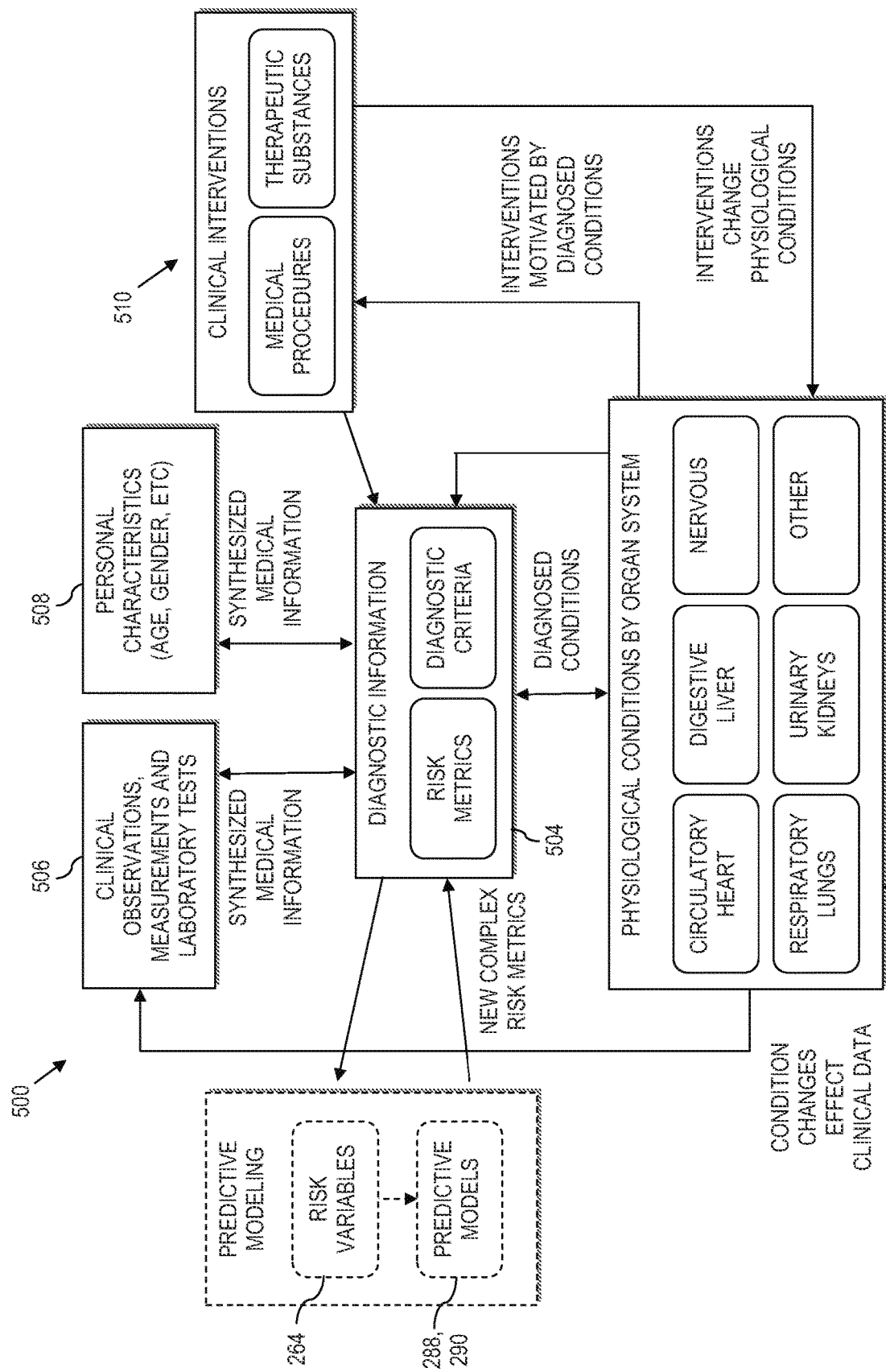
FIG. 5 is a conceptual model of a clinical environment employed for knowledgebase construction, according to aspects of the present disclosure.

Referring to FIG. 5, a model environment 500 is shown in relation with certain elements of the system of FIG. 2A and FIG. 2B. That is, the illustrative model environment 500 excludes the predictive modeling process (risk variables 264 and predictive models 288, 290 of FIG. 2B).

In general, the model environment 500 represents a setting where clinicians operate. That is, the model environment 500 conceptualizes how doctors and other clinicians actually work within the physical clinical environment to treat patients. In this regard, the model environment 500 defines the types of information necessary to be captured, in order to lead to the construction of an ontology, which allows an underlying knowledgebase to be populated.

In the illustrative example, the model environment 500 includes a physiology organizing process 502. The physiology organizing process at 502 serves as a starting point where a physiological condition of interest is identified. In practice, the model approach of FIG. 5 can be extended to multiple physiological conditions of interest. Accordingly, in an example implementation, physiological conditions are organized by organ system, e.g., categorized into circulatory, respiratory, digestive, urinary, nervous, other, etc. The physiological conditions of interest represent information that may not be observed. Rather, these conditions represent the subject matter that the model is trying to understand.

To address how the physiological condition of interest is diagnosed, a diagnostic information process 504 is implemented. The diagnostic information process at 504 attempts to identify the diagnosed conditions by evaluating and generating diagnostic data comprised of risk metrics and diagnostic criteria. The diagnostic criteria define criteria such as symptoms and rules utilized in diagnosing the physiological condition of interest. Correspondingly, a risk metric is a metric employed by a diagnostic criterion to assess risk. The diagnostic information may also comprise contributing conditions that may be associated with related physiologies.

In order to evaluate risk metrics and diagnostic criteria, the diagnostic process 504 interacts with medical observational data. For instance, as illustrated, medical observational data comprises clinical information 506 and personal information 508. The interactions with the medical observational data are focused on where to look in the medical records to find the relevant information to evaluate diagnostic criteria and risk metrics for the physiological condition of interest.

The clinical information 506 comprises electronic records that store information such as clinical observations, measurements and laboratory tests. The personal information at 508 comprises electronic records that store personal characteristics, e.g., age, gender, etc. In this regard, the clinical information 506 and the personal information at 508 represent an environment that a clinician is operating in, and thus represent an environment that the clinician gets to observe. As such, the clinical information 506 and personal information 508 can be used to stratify how to look at patients. A feedback from the physiological conditions process 502 to the clinical information 506 represents an opportunity for condition changes to effect changes in the observed clinical data.

The diagnostic information process 504 provides inputs into predictive modeling, such as that described with reference to FIG. 2A and FIG. 2B. For instance, the risk metrics and diagnostic criteria can be used to identify candidate model risk variables (see for instance, the risk variables 264 of FIG. 2B). As noted in greater detail herein, the risk variables can impact the generation of predictive models (see baseline outcome likelihood model 288 and dynamic outcome likelihood model 290 of FIG. 2B). In turn, the modeling process of FIG. 2A and FIG. 2B can feed back new (complex) risk metrics to the diagnostic information process 504.

To address whether there are candidate interventions, the physiological condition process 502 interacts with a clinical interventions process 510. As with the clinical information 506 and the personal information at 508, the interventions process 510 represents an environment that a clinician is operating in, and thus represents an environment that the clinician gets to observe. Interventions motivated by diagnosed conditions may be used to identify medical procedures and therapeutic substances that may be relevant to the physiological condition of interest. Also, interventions may change the underlying physiological conditions. To address whether there are any related physiologies, the physiological conditions process 502 feeds back to the diagnostic information 504 to explore whether there are other diagnosed conditions that may affect the current physiological condition of interest. By way of example, impaired pulmonary function may affect kidney failure.

The model environment 500 is used to construct an ontology. Medical observational data may be synthesized from the combination of clinical information 506 and personal information 508, into diagnostic information 504.

Figure 6:
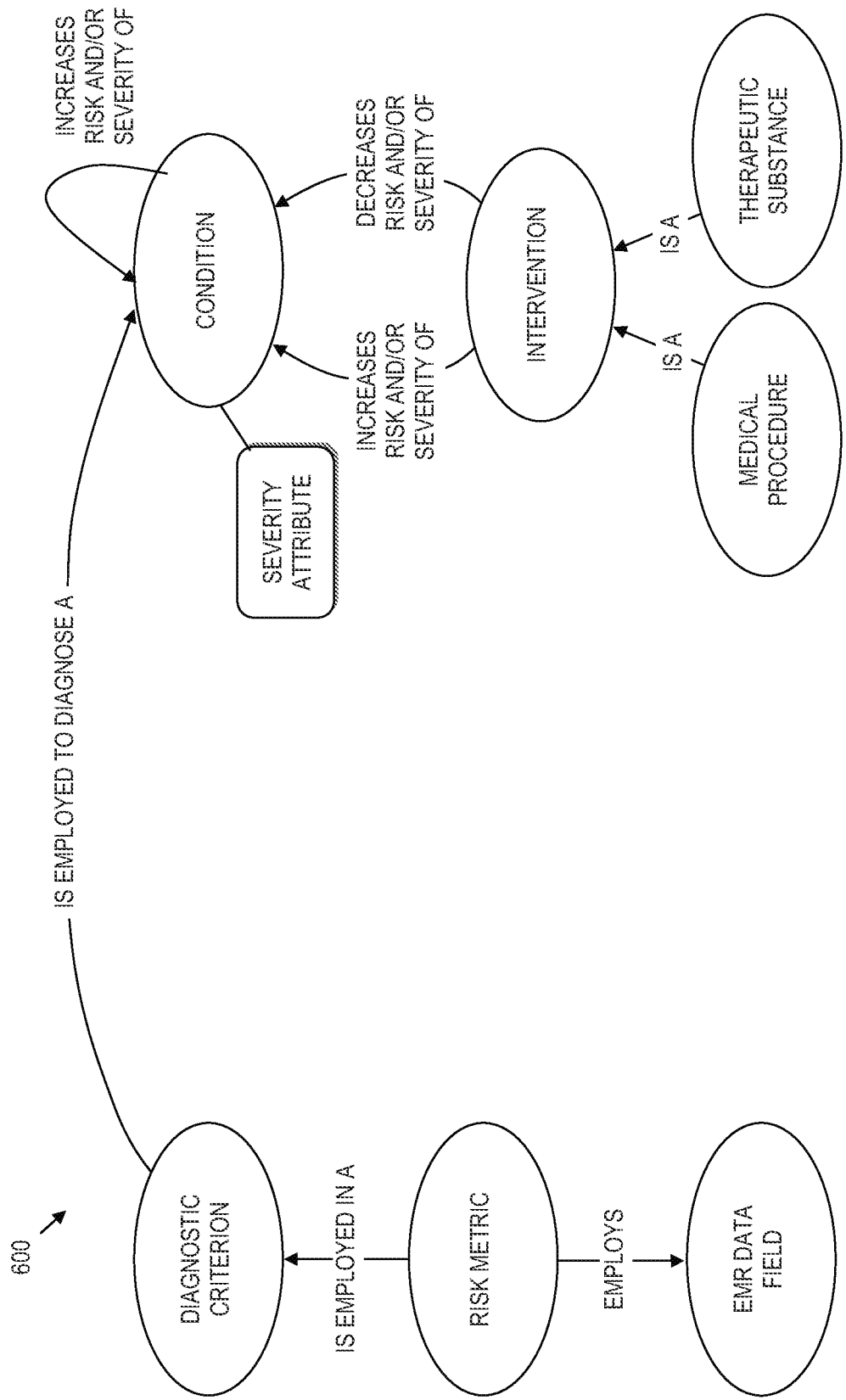
FIG. 6 is an illustration of a knowledgebase ontology for capturing diagnostic and interventional knowledge related to physiological conditions, according to aspects of the present disclosure.

Ontology:

Referring to FIG. 6, the multi-conditional model framework of FIG. 5 is an example organization that allows the construction of the ontology for a clinical knowledgebase 600. The clinical knowledgebase 600 is an information repository that provides a means for clinical information to be collected, organized, shared, searched and utilized. In this manner, the contents of the clinical knowledgebase 600 are controlled by an ontology that is constructed to represent the clinical setting modeled in FIG. 5.

In the illustrative embodiment, the ontology defines what types of triples are allowed in the knowledgebase. The illustrated triple types are set up with entity relationships that not only build knowledge into the knowledgebase, but also provide for a recursive way to harvest domain knowledge from the clinical environment (such as the multi-conditional model framework of FIG. 5 and corresponding method 700 of FIG. 7) for the physiological condition of interest and for related physiological conditions of interest. In this manner, the entities (concepts) allow only certain types of relationships to connect entities (connect concepts). An example set of entity-relationship-entity triple types are illustrated in Table 1, below.

TABLE 1

Triple Relationship Types

| Entity | Relation | Entity |
| --- | --- | --- |
| Diagnostic criterion | Is employed to diagnose a | Condition (severity attribute) |
| Intervention | Increases risk and/or severity of | Condition (severity attribute) |
| Intervention | Decreases risk and/or severity of | Condition (severity attribute) |
| Risk metric | Employs | EMR data field |
| Medical procedure | Is an | Intervention |
| Therapeutic Substance | Is an | Intervention |

The illustrated ontology includes several entity types, including for instance, diagnostic criterion, risk metric, electronic medical record (EMR) data field, condition, intervention, medical procedure and therapeutic substance. As illustrated in Table 1 and FIG. 6, the triple types are configured in a manner that logically follows the organization of the multi-conditional model framework of FIG. 5. For instance, medical procedures and therapeutic procedures relate to interventions. Likewise, interventions and diagnostic criteria relate to physiological conditions of interest. Risk metrics relate to diagnostic criteria. Electronic medical record data or data from other electronic data sources are employed by, or are recorded in risk metrics.

Figure 7:
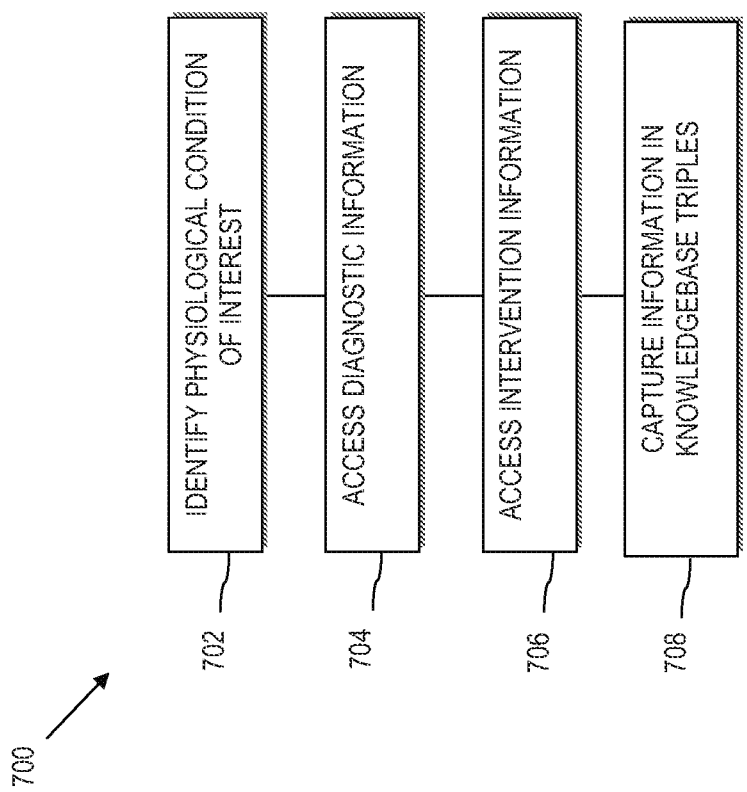
FIG. 7 is a method of collecting knowledge to populate a knowledgebase, according to aspects of the present disclosure.

Building the Knowledge Base:

Referring to FIG. 7, knowledge about the model 500 in FIG. 5 can be obtained by a method 700 for populating a clinical knowledgebase. The method 700 includes numerous steps of a technical character that solve, among other issues, accessing relevant information and capturing that information in the form of knowledgebase triples.

Features that provide an inventive technical contribution include identifying a specific physiological condition of interest associated with the adverse outcome type at 702. The method 700 also comprises accessing diagnostic information at 704 (e.g., the diagnostic information 504 of FIG. 5), accessing intervention information at 706 (e.g., the intervention information 510 of FIG. 5) and populating a triple of a knowledgebase at 708. For instance, accessing diagnostic information at 704 may be implemented by obtaining diagnostic information based upon the identified specific physiological condition. Likewise, accessing intervention information at 706 may be implemented by obtaining clinical intervention information that is likely to include appropriate interventions for the physiological condition of interest. Moreover, populating the knowledgebase at 708 may be implemented by populating a knowledgebase that relates the obtained diagnostic information to the physiological condition of interest and that relates the obtained clinical intervention information to the physiological condition of interest. Knowledge from the populated knowledgebase may be used to guide the selection of a set of candidate model variables for predicting the likelihood of an adverse health outcome.

In an illustrative implementation, diagnostic information may be obtained by identifying diagnostic criteria employed to diagnose the physiological condition, identifying contributing conditions to the physiological condition, identifying corresponding risk metrics of the identified diagnostic criteria, and identifying electronic medical record data fields or other electronic data sources necessary to employ the diagnostic criteria. Likewise, clinical intervention information may be obtained by identifying at least one of medical procedures and therapeutic substances employed to treat the specific physiological condition of interest and identifying at least one of medical procedures and therapeutic substances employed to treat other physiological conditions that also have an effect on the risk/severity of the physiological condition of interest. The method 700 may also include utilizing an ontology of triple types allowed by the knowledgebase to identify queries to elicit diagnostic information and clinical intervention information to build the knowledgebase.

According to still further aspects of the present disclosure, the ontology defining the types of triples allowed in the knowledgebase 600 can be used to drive the questions asked against the model of FIG. 5 in order to elicit relevant information necessary to populate the knowledgebase with triples. Questions defined by the entity-relationship-entity triple structure are employed to define the questions for conditions, intervention, and risk metrics, etc., that make up the knowledgebase 600. A clinician can build the knowledgebase 600 by starting with a physiological condition of interest (e.g., see also the physiological condition process 502 of FIG. 5). By way of example, the clinician may start with pneumonia, acute kidney injury, sepsis, etc.

The clinician considers the first inquiry discussed above with regard to FIG. 5, i.e., how is the physiological condition of interest diagnosed? (See also, the diagnostic information process 504 of FIG. 5.) To answer this inquiry, the clinician is led to populate the (Diagnostic Criterion, IS EMPLOYED TO DIAGNOSE A, Condition) triple type. This leads the clinician to populate the (Risk Metric, IS EMPLOYED IN A, Diagnostic Criterion) triple type and the (Risk Metric, EMPLOYS, EMR Data Field) triple type. As an example, a Risk Metric may be derived from one or more of the clinical observations 506 and personal characteristics 508 of FIG. 5 as captured in EMR Data Fields or other electronic data source.

The clinician then considers the second inquiry discussed above with regard to FIG. 5, i.e., whether there are candidate interventions to address the physiological condition? (See also, the Clinical Intervention process 510 of FIG. 5.) To answer this inquiry, the clinician is lead to populate (Intervention, INCREASES RISK AND/OR SEVERITY OF, Condition) and (Intervention, DECREASES RISK AND/OR SEVERITY OF, Condition) triple types. Intervention types may be more specifically defined via the (Intervention, IS A, Medical Procedure) and (Intervention, IS A, Therapeutic Substance) triple types.

The clinician then considers the third inquiry discussed above with regard to FIG. 5, i.e., whether there are any related physiologies? To answer this inquiry, the clinician is lead to consider, for instance, other physiological conditions that affect the risk and/or severity of the physiological condition of interest. If so, the clinician loops back and repeats the entire above-described process for the related physiological conditions until all related physiological conditions have been exhausted. For example, assume that the clinician is evaluating acute kidney injury (AKI). After the clinician populates the triples related to AKI, the clinician recognizes, by way of example, that impaired pulmonary function may affect kidney failure. As such, the clinician loops back and populates the triples related to impaired pulmonary function. The above-iterative process can repeat until all physiological conditions of interest have been captured in the knowledgebase. Thus, the knowledgebase can grow in a decided and controlled manner. Moreover, the clinician can periodically update the knowledgebase triples, e.g., to reflect changes in the underlying knowledge.

According to various aspects of the present disclosure, the entities (e.g., Conditions, Interventions, etc.) can have attributes that further define relevant information. By way of example, a condition such as AKI may have an attribute to designate severity level 1, severity level 2, severity level 3, etc. Still further, any entity can have attributes and other related information associated therewith. Also, the values for the entities that define triples can be simple or complex. For instance, an entity may be expressed as: "condition 1<X and condition 2>Y". The relationship may be "leads to" and the relational entity may have a value "AKI level 1".

By implementing the construction of the knowledgebase 600 in the manner described above, the knowledgebase is strongly correlated with human physiology and provides a basis for incorporating physiology into predictive models for outcome likelihood to give these models a physiological basis as opposed to only an empirical, correlational basis. Thus, subject matter content is built into predictive models.

Application of the Knowledge Base:

By way of illustration, the performance of candidate model variable selection (e.g., selecting the candidate model variables at 252 of FIG. 2B) may be carried out by querying the knowledgebase 600 to identify triples that are associated with the physiological condition related to the adverse outcome of interest. For instance, a process may build a list of triples that are associated with acute kidney injury (AKI). From the list of triples, a set of candidate model variables can be identified.

As yet another illustrative example, the alerting and attribution process (described with reference to FIG. 3B) can query the knowledgebase 600 to determine recommendations for mitigation actions, for attribution information, possible interventions, etc. For instance, a system can provide intervention information by accessing the triples of the knowledgebase 600 with entity relationships linked to the Intervention entity type.

Still further, the knowledgebase 600 can be used to determine an etiological model (e.g., used to define the outcome specific etiological knowledge 206 of FIG. 2B). For instance, a system may extract from the knowledgebase, all information with regard to AKI. That knowledge can be utilized as the etiological model.

According to aspects of the present disclosure, the knowledgebase allows the implementer to define risk variables that tie conditions to attributions, giving meaning to the identified attributions. For instance, a process comprises selecting a risk variable. The process can make the risk variable more physiologically meaningful by attributing the collected information to physiologically meaningful information, which improves the quality of attribution with recommendations compared to purely analytical modeling which may not be able to directly tie a risk variable to a physiological condition.

Figure 8:
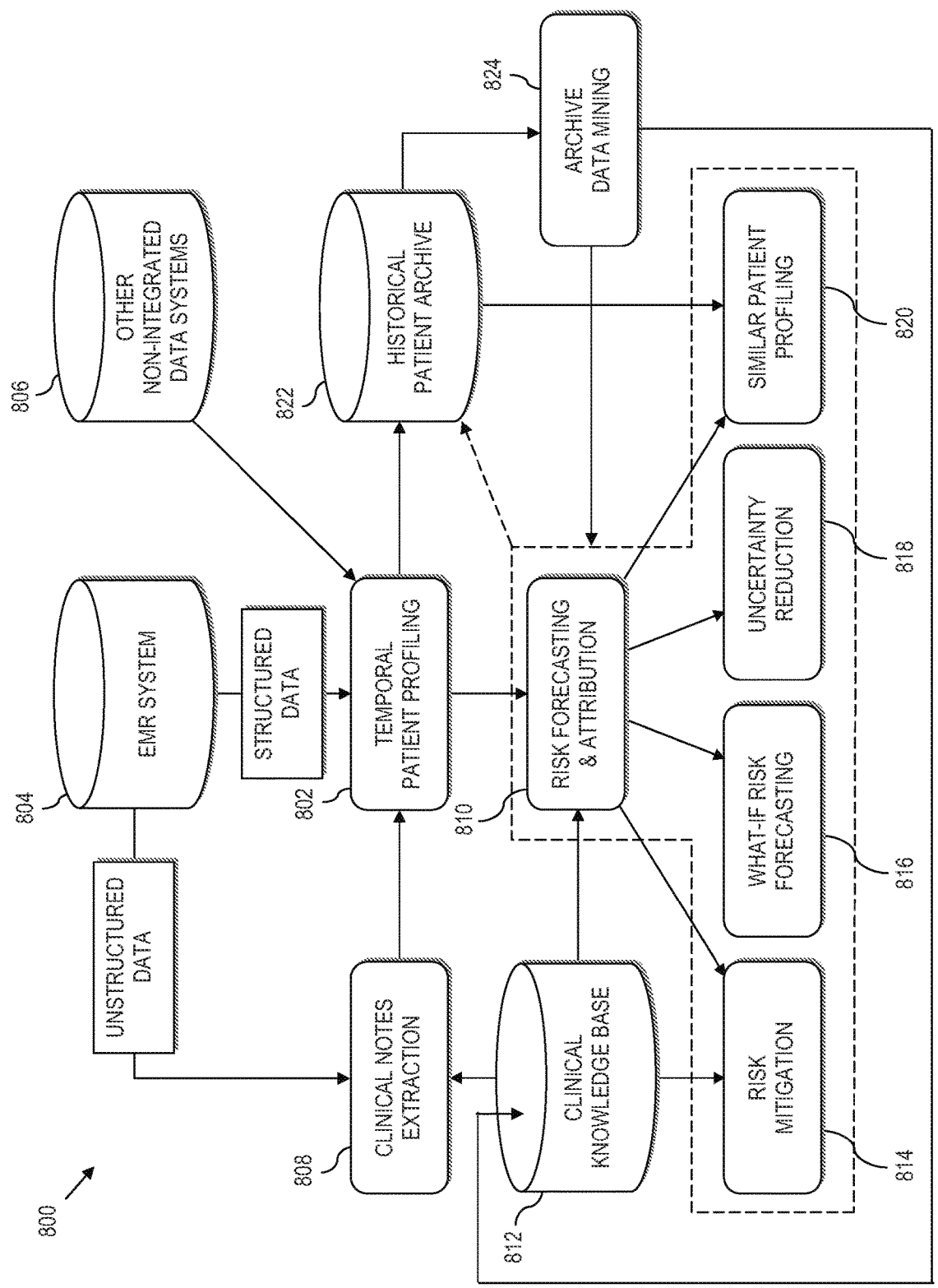
FIG. 8 is a clinical predictive analytics system according to aspects of the present disclosure.

Clinical Predictive Analytics System:

Referring to FIG. 8, a view is provided, which defines a Clinical Predictive Analytics System according to aspects of the present disclosure. The Clinical Predictive Analytics System can be used to leverage the knowledgebase 600 in several unique applications, which each address a different application for a clinician.

System processing begins with a temporal patient profiling process 802, which extracts relevant structured data from an electronic medical records (EMR) system 804 and other non-integrated data systems 806 to build temporal patient profiles. In this regard, the data systems 806 that are not yet integrated with the EMR system 804 may yield important patient data that can also be used by the temporal patient profiling process 802 to build patent profiles.

However, all the relevant EMR data from the EMR system 804 will not likely be in structured form. Therefore, text extraction is performed on clinical notes, e.g., via a clinical notes extraction process 808 to enhance the temporal patient profiles. The extraction process 808 employs a proprietary clinical knowledgebase to target and capture relevant clinical terminology within the clinical notes.

A central system function is performed by the risk forecasting & attribution process 810. Competing risks associated with multiple adverse outcomes are characterized and overall risk is attributed to adverse outcome types and causal factors. The clinical knowledgebase 812 (equivalent to knowledgebase 600 in FIG. 6) is employed to identify the candidate model risk variables to include in the risk forecasting models. The central system function is then supplemented with four secondary functions.

Risk Mitigation:

The system 800 also provides risk mitigation information 814 in the form of candidate interventions. Here the clinical knowledgebase 812 is employed to link identified causal factors to underlying conditions and then to candidate interventions.

What-If Analysis:

The system 800 also supports what-if risk forecasting 816. Here, candidate interventions or other anticipated changes (i.e., changes outside candidate interventions) in patient care can be entered into the system 800 to determine (e.g., predict) the changes in risk that will occur as a result of considered changes in patient care.

According to aspects of the present disclosure, the What-If component provides a single patient risk analysis. In general, a What-If process allows a clinician to anticipate or otherwise simulate interventions. In an illustrative example, relevant data, e.g., the ERM system 804 of FIG. 8, clinical observations 506 and personal characteristics 508 of FIG. 5, the database 306 of FIG. 3, etc.) may be copied to a simulation environment. By simulating an intervention, data in the underlying simulation environment is updated with temporary or simulated data. Based upon the simulated intervention, the change to the underlying data in the simulation environment causes the risk factors to be updated. As a result, the baseline and dynamic outcome likelihoods will change, thus affecting the risk determination. By simulating one or more interventions (such as in a suitable simulation environment), the clinician can not only explore the effect of the intervention on risk, but also see the attributing risk factors based upon the knowledge contained in the knowledgebase.

Accordingly, the system changes the underlying data, e.g., within the simulation environment, according to the What-If analysis proposed by the user, e.g., using a GUI. The change to the underlying data percolates through the system and updates the risk variables. The updated risk variables drive the alerting and attribution (e.g., analogous to the process 316 of FIG. 3), thus forecasting not only the likely outcomes but also the attributing factors to increases or decreases in risk.

Because the knowledgebase includes triples that associate related physiological conditions, the What-If analysis affects the total risk for a patient. Accordingly, the clinician can explore issues such as whether to stop a medication, apply a treatment, etc.

Uncertainty Reduction/Value of Information Analysis:

The system 800 also supports uncertainty reduction 818. Here, forecasted risks have associated uncertainties and in some cases the uncertainties can be effectively reduced by obtaining new clinical data. In these situations, the system 800 may recommend prioritized new clinical data types that will likely lead to the greatest uncertainty reduction.

According to aspects of the present disclosure herein, a process is provided that creates an assessment of missing information. The missing information assessment allows the system to evaluate impact of the missing data and compute the uncertainty reduction that will occur if certain missing pieces of information are obtained.

Similar Patient Profiling:

The system 800 still further supports similar patient profiling at 820. Recognizing that few things resonate with clinicians like case studies of actual patient experiences, the system 800 includes a historical patient archive 822 with full temporal histories on previous patients for which outcomes are known. Given a patient of interest, aggregated patient histories for groups of "similar" patients are presented in a manner that supports clinical decision-making. This could include characterizations of intervention methods used and the effectiveness of mitigating adverse events.

For instance, a method of implementing similar patient profiling, comprises collecting electronic patient data about an actual patient to be monitored for an adverse outcome. The method also comprises determining risk variables from the collected electronic patient data, where the risk variables are selected to be predictive of the adverse outcome of interest (e.g., where the risk variables are involved in at least one of a baseline outcome likelihood model and dynamic outcome likelihood model for the adverse outcome to identify a patient profile). Still further, the method comprises extracting electronic patient data for historical patients having a profile that matches the identified patient profile, and presenting de-identified information from at least one patient history corresponding to a historical patient that matches the identified patient profile.

The method may also comprise extracting electronic patient data from a historical patient archive with full temporal histories on previous patients for which outcomes are known. Still further, the method may comprise identifying at least one previous type of intervention for a similar patient, and presenting the outcomes of each type of intervention (e.g., by presenting results related to the actual outcomes of each type of intervention).

Learning System:

Patient-related data from the decision-support part of the system 800 is also captured in the electronic records of a historical patient archive. Thus, the system can associate outcome evidence back to decisions made. Archive data 824 is mined for at least two purposes, e.g., to improve the predictive models and algorithms employed for clinical decision support, and for new clinical knowledge that can be added to the clinical knowledgebase.

Clinical Training Similarity:

According to illustrative aspects of the present disclosure, a clinical training similarity process is provided. When presented with a patient, the system generates a historical set of patients to employ as a basis for a simulated training exercise. The system uses a profile of the patient to find a history of prior patients having a matching profile.

The group of located historical matching patients are employed to evaluate the likely outcome(s) of interventions selected by the trainee. The simulated training exercise can be iteratively repeated and the collective results of a set of exercises are made available for scrutiny and evaluation. The clinical training similarity can be used to provide confidence in an actual diagnosis and prescribed intervention.

For instance, a method of implementing clinical training similarity, comprises collecting electronic patient data about actual patients monitored for an adverse outcome. The method also comprises determining risk variables from the collected electronic patient data, where the risk variables were selected to be predictive of the adverse outcome of interest (e.g., where the risk variables are involved in at least one of a baseline outcome likelihood model and dynamic outcome likelihood model for the adverse outcome to identify patient profiles). The method also comprises evaluating interventions recommended by the trainee based on the actual histories of prior patients having a matching profile.

The method may also comprise comparing a group of located historical matching patients to evaluate the risk(s) and outcome(s) of those patients that followed a trajectory of the trainee-proposed intervention, to those that received alternative interventions. Also, the method may comprise identifying patient profiles of similar patients in the historical patient archive.

Multiple Outcome:

According to still further aspects of the present disclosure, the system 800 may contain a layer that aggregates the risk associated with multiple outcomes into a single measure. The data that percolates up to the single measure may be an accumulation of the risk associated with each grouped outcome. For instance, assume that three adverse outcomes comprising sepsis, pneumonia and AKI are defined as a group associated with a single measure of risk. That single measure may be defined as an accumulation of the risks associated with any of sepsis, pneumonia and/or AKI. Thus, the combined risk of the members of the group may be compared to a threshold (e.g., analogous to the alerting and attribution process 316 of FIG. 3).

As yet another illustrative example, the single risk measure may be defined as a risk value associated with any one of the members. For instance, an action may be triggered if the risk associated with any one of the members of the group exceeds a predetermined threshold (e.g., analogous to the alerting and attribution process 316 of FIG. 3). Still further, the multiple outcome risk assessment process may be implemented by a combination of the above-described techniques.

According to further aspects of the present disclosure herein, if an alert is triggered, (e.g., analogous to the alerting and attribution process 366 of FIG. 3B), then the clinician can drill down through the single measure into the details, e.g., to explore and analyze any one or more outcomes of the group, using any of the techniques set out in greater detail herein.

Continuous Risk:

As described in greater detail above, risk may be expressed as a step indicator, e.g., level 1, level 2, level 3 . . . , etc. The step function of risk may also be replaced with a continuous function where risk values fall on the continuum.

Miscellaneous:

According to aspects of the present disclosure, a system is provided, which identifies at-risk patients in time to take mitigative action. The system computes the likelihood of each type of risk. Moreover, the model used to develop the likelihood of each type of risk can be iteratively improved upon such that the model can be refined over time to improve the quality of the likelihood computations and associated risk estimates. Moreover, the system identifies driving risk factors for at-risk patients to assist medical staff in identifying mitigative actions. That is, the system tells clinical staff driving factors behind the risk.

A GUI display facilitates comparison of outcome likelihoods across all possible clinical conditions of interest. The system mines electronic health record data and uses adverse event-focused predictive models to give clinicians near real-time, patient specific risk and contextual information. The predictive analytics will improve over time with additional data. Moreover, the model design is separate from the clinical application and can thus easily receive periodic updates. Also, model fitting can be continuously improved based upon model scoring.

The system can provide output from a single outcome perspective, which can include for instance, estimated outcome likelihoods, binary alert indicators and attribution of risk to contributing risk factors. The system can also provide output from multiple perspectives, including for instance, estimated likelihoods of any adverse outcome, binary alert indicators for any adverse outcome and attribution of total risk for all adverse outcomes.

According to aspects of the present disclosure, the system is capable of identifying data quality issues, which can be utilized to facilitate improvement in the models. That is, the model design phase (e.g., as described in FIG. 4) and the clinical application (e.g., as described in FIG. 3) can iterate and update based for instance, on the scoring computed by the alerting and attribution algorithms (e.g., as described in FIG. 4). Thus, there can be a push back into the data generation process to improve the quality of the data. This allows the system to continually improve the manner in which the system identifies driving risk factors for at-risk patients to assist medical staff in identifying mitigative actions.

According to further aspects of the present disclosure, issues of dealing with adverse outcomes are essentially "bookended" by providing on one side, a solution that helps health care facilities make policy decisions to change patient care procedures and on the other side, a solution that evaluates historical events to help a person or team attending a patient make real time decisions about the healthcare applied to that patient.

According to aspects of the present disclosure, the system is capable of running a simulation of a historical patient care scenario using data from the patient archive or other sources to provide a training environment for care staff to assess and evaluate clinical decision making of an individual user. This training environment may allow a user to select interventions and then observe both the simulated outcome based on their selections as well as what actually happened in the original patient care scenario.

Figure 9:
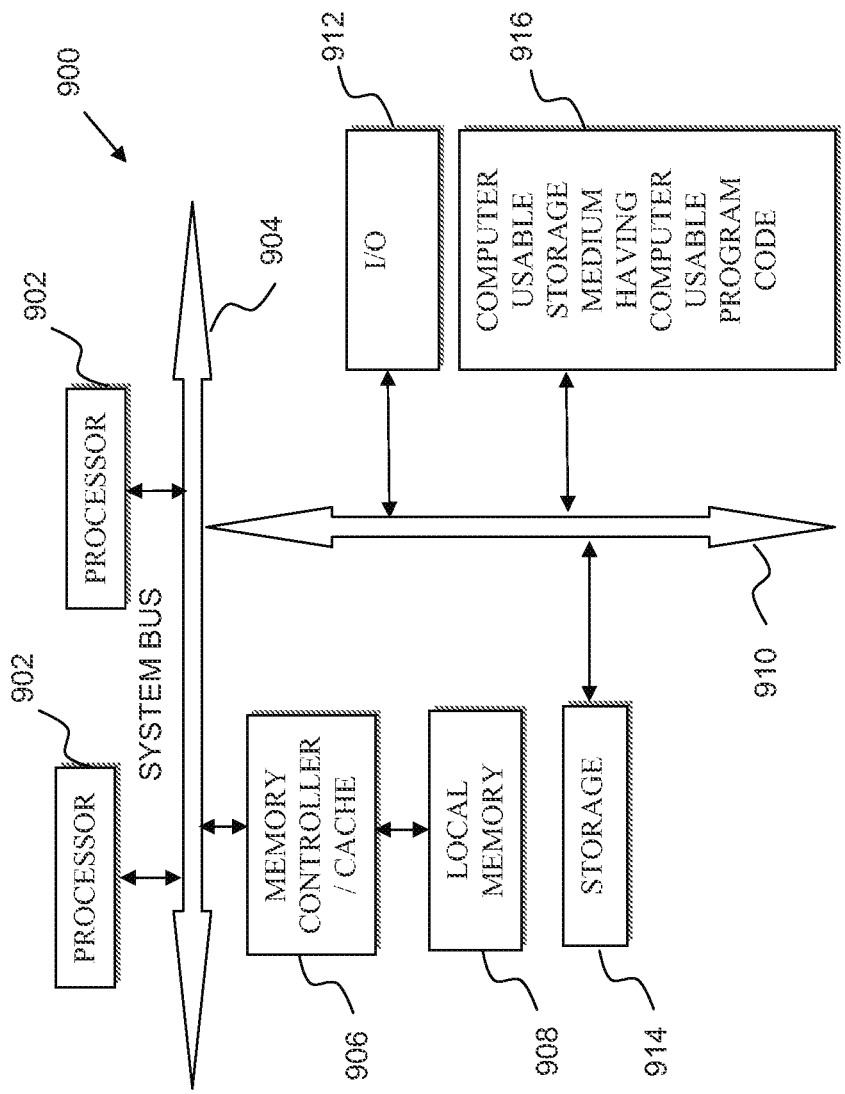
FIG. 9 is a block diagram of a computer system for implementing the flows of any of the previous FIGURES, according to aspects of the present disclosure.

Example Computer Implementation:

Referring to FIG. 9, a block diagram of a data processing system is depicted in accordance with the present disclosure. Data processing system 900 may comprise a one or more processors 902 connected to system bus 904. Also connected to system bus 904 is memory controller/cache 906, which provides an interface to local memory 908. An I/O bus 910 is connected to the system bus 804 and provides an interface to I/O devices 912, such as input output devices (I/O devices), storage, network adapters, graphic adapters, etc.

Also connected to the I/O bus 910 may be devices such as one or more storage devices 914 and a computer usable storage medium 916 having computer usable program code embodied thereon. The computer usable program code may be executed, e.g., by the processor(s) 902 to implement any aspect of the present disclosure, for example, to implement any aspect of any of the methods, processes and/or system components illustrated in FIGS. 1-8.

As will be appreciated by one skilled in the art, aspects of the present disclosure may be embodied as a system, device or method. Furthermore, any combination of one or more computer readable medium(s) may be utilized. The computer readable medium may be a computer readable signal medium or a computer readable storage medium. For instance, a computer readable signal medium may include a propagated data signal with computer readable program code embodied therein, for example, in baseband or as part of a carrier wave. Comparatively, aspects of the present disclosure may take the form of a computer program product embodied in one or more computer readable storage medium(s) (i.e., computer readable storage hardware) having computer readable program code embodied thereon. As used herein, a computer readable storage medium may be any tangible hardware medium that can contain or store a program for use by or in connection with an instruction execution system, apparatus, or device.

Exemplary and non-limiting structures for implementing a computer readable storage medium include a portable computer diskette, a hard disk, a random access memory (RAM), Flash memory, a read-only memory (ROM), a portable compact disc read-only memory (CD-ROM), digital video disk (DVD), an optical storage device, a magnetic storage device, or any suitable combination of the foregoing.

Aspects of the present disclosure are described herein with reference to flowchart illustrations and/or block diagrams of methods, apparatus (systems) and computer program products according to embodiments of the disclosure. Each block of the flowchart illustrations and/or block diagrams, and combinations of blocks in the flowchart illustrations and/or block diagrams, can be implemented by computer program instructions, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Each block in the flowchart or block diagrams of the FIGURES herein, may represent a module, segment, or portion of code, which comprises one or more executable instructions for implementing the specified logical function(s). However, the functions noted in the block may occur out of the order noted in the figures. For example, two blocks shown in succession may, in fact, be executed substantially concurrently, or the blocks may sometimes be executed in the reverse order, depending upon the functionality involved.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. Further, the terms "comprises" and "comprising," when used in this specification, specify the presence of stated features, steps, operations, elements, and/or components, but do not preclude the presence or addition of one or more other features, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure.

Having thus described the disclosure of the present application in detail and by reference to embodiments thereof, it will be apparent that modifications and variations are possible without departing from the scope of the disclosure defined in the appended claims.

What is claimed is:

1. A computer-implemented process for performing a clinical assessment, comprising:
    implementing a data abstraction process that receives as input, electronic patient data about a patient of interest from a first data source, and transforms at least a portion of the received input to standardized format patient data for the patient of interest, which is stored in a second data source;
    matching the standardized format patient data for the patient of interest to a set of risk variables, where the risk variables include at least one variable classified into a baseline group composed of risk variables that are non-modifiable based on provided medical care of a corresponding patient, and at least one variable classified into a dynamic group composed risk variables that are modifiable based on the provided medical care of the corresponding patient, where the set of risk variables are selected to be predictive of an adverse outcome of interest associated with a physiological condition;
    extracting by a processor, a set of outcome models, the set of outcome models corresponding to the adverse outcome type associated with the physiological condition of interest, the set of outcome models including a baseline outcome likelihood model extracted from a first computer memory and a dynamic outcome likelihood model extracted from a second computer memory, wherein a model of the set of outcome models is generated using a first training data set comprising electronic patient training data transformed from a proprietary format to a standardized generic data format and extracted from a computer storage device, where the selection process automatically selects risk variables that are classified into the baseline group and the dynamic group;
    applying the set of risk variables to the set of outcome models to generate a baseline outcome likelihood and a dynamic outcome likelihood;
    aggregating patient histories for groups of patients similar to the patient of interest;
    determining whether at least one of the baseline outcome likelihood and dynamic outcome likelihood exceeds a predetermined threshold;
    facilitating an intervention in treating the physiological adverse outcome type associated with the physiological condition of interest by including an attribution associated with at least one risk factor causing the predetermined threshold to be exceeded;
    verifying an effectiveness of the intervention based on the aggregated patient histories for the groups of patients similar to the patient of interest; and
    outputting an electronic alert to a remote electronic device to alert a clinician if at least one of the baseline outcome likelihood and dynamic outcome likelihood exceeds the predetermined threshold, the alert providing the intervention.

2. The process of claim 1, wherein:
    at least one variable classified into the dynamic group is updated as new data becomes available for the patient of interest.

3. The process of claim 1 further comprising:
    detecting that a select risk variable for which corresponding electronic patient data about the patient of interest is missing; and
    imputing a value to the missing data based upon other risk variables having corresponding electronic patient data with known values, where the other risk variables correlate with the missing risk variable.

4. The process of claim 1 further comprising:
    performing retrospective risk attribution for a population of patients comprising:
        performing computations to produce risk attribution vectors that apply to groups of patients rather than single patients;
        utilizing the attribution vectors to draw conclusions across the population as to the likely root cause(s) that lead to eventual adverse outcomes in the patient data; and
        utilizing the identified root causes to facilitate clinical policy decisions designed to reduce the incidence rate for adverse patient outcomes.

5. The process of claim 1 further comprising:
    generating an output to the remote electronic device, the output conveying risk mitigation information in the form of candidate interventions by outputting to the remote electronic device:
        identified causal factors linked to underlying patient physiological conditions; and
        candidate interventions based on clinical knowledge extracted from a populated clinical knowledgebase.

6. The process of claim 1 further comprising:
    performing what-if risk forecasting by:
        simulating at least one intervention;
        updating the estimated baseline outcome likelihood and a dynamic outcome likelihood based upon temporary changes to risk variable values required to simulate the intervention; and
        identifying whether the patient risk changes based upon the updates to the estimated dynamic outcome likelihood.

7. The process of claim 1 further comprising:
    associating uncertainty to forecasted risk based upon the baseline outcome likelihood and the dynamic outcome likelihood;

creating an assessment of missing information;
evaluating the impact of the missing data;
computing an uncertainty reduction that will occur if certain missing pieces of information are obtained; and
generating an output to the remote processing device, prioritized new clinical data types that will likely lead to the greatest uncertainty reduction.

8. The process of claim 1 further comprising:
extracting electronic patient data for historical patients having a profile that matches the identified patient profile, and
presenting the identified information from at least one patient history corresponding to a historical patient that matches the identified patient profile.

9. The process of claim 8 further comprising:
extracting electronic patient data from a historical patient archive with full temporal histories on previous patients for which outcomes are known; and
identifying at least one previous type of intervention for a similar patient, and presenting the outcomes of each type of intervention.

10. The process of claim 1 further comprising:
collecting electronic patient data about actual patients monitored for an adverse outcome;
determining risk variables from the collected electronic patient data, where the risk variables are selected to be predictive of the adverse outcome of interest;
identifying patient profiles of similar patients that are in a historical patient archive; and
evaluating recommended interventions based on the actual histories of the identified patient profiles of similar patients in the historical patient archive.

11. The process of claim 10 further comprising:
comparing a group of located historical matching patients to evaluate the risk(s) and outcome(s) of those patients that followed a trajectory of a select recommended intervention, to those that received alternative interventions.

12. The process of claim 1 further comprising:
implementing in a clinical computer processing environment, a model generating process that comprises:
generating, by an automated computer-implemented selection process, an outcome likelihood model form that evaluates a likelihood of the adverse outcome type associated with the physiological condition of interest, using a first training data set comprising electronic patient training data extracted from a computer storage device, where the selection process automatically selects risk variables that are classified into the baseline group and the dynamic group;
generating dynamic risk variable model forms that predict values for risk variables in the dynamic group as a function of at least one of the risk variables in the baseline group;
generating a baseline outcome likelihood model form associated with the adverse outcome type using the outcome likelihood model form and the dynamic risk variable model forms;
generating a dynamic outcome likelihood model form associated with the adverse outcome type using the outcome likelihood model form and at least one of the selected risk variables; and
fitting the constructed outcome likelihood model form, baseline outcome likelihood model form, and dynamic outcome likelihood model form, to a second training data set comprising electronic patient training data stored in at least one database that includes both outcome data and data values that correspond to the selected risk variables, to produce the set of outcome models including the baseline outcome likelihood model and the dynamic outcome likelihood model.

13. A computer-implemented process for triggering an alert responsive to an adverse health likelihood, comprising:
implementing a first data abstraction process that receives as input, electronic patient data about a first patient population, and transforms at least a portion of the received input to standardized format patient data, which is stored as a first training data set;
implementing a second data abstraction process that receives as input, electronic patient data about a second patient population, and transforms at least a portion of the received input to standardized format patient data, which is stored as a second training data set;
training an outcome likelihood model form using the first training data set, by an automated computer-implemented selection process, where the outcome likelihood model form evaluates a likelihood of an adverse outcome type associated with a physiological condition of interest, where the selection process automatically selects risk variables, wherein the selected risk variables are classified into a baseline group composed of risk variables that are non-modifiable based on provided medical care of a corresponding patient, and a dynamic group composed risk variables that are modifiable based on the provided medical care of the corresponding patient, wherein the outcome likelihood model is generated using a first training data set comprising electronic patient training data transformed from a proprietary format to a standardized generic data format and extracted from a computer storage device, where the selection process automatically selects risk variables that are classified into the baseline group and the dynamic group;
generating dynamic risk variable model forms from the selected risk variables that predict values for risk variables in the dynamic group as a function of at least one of the risk variables in the baseline group;
generating a baseline outcome likelihood model form associated with the adverse outcome type using the outcome likelihood model form and the dynamic risk variable model forms;
generating a dynamic outcome likelihood model form associated with the adverse outcome type using the outcome likelihood model form and at least one of the selected risk variables;
fitting the constructed outcome likelihood model form, baseline outcome likelihood model form, and dynamic outcome likelihood model form, to the second training data set comprising electronic patient training data stored in at least one database that includes both outcome data and data values that correspond to the selected risk variables, to produce an outcome likelihood model stored in a first computer memory, a baseline outcome likelihood model stored in a second computer memory, and a dynamic outcome likelihood model stored in a third computer memory;
collecting by a computer, electronic patient data about an actual patient seeking medical treatment from at least one electronic data source;
automatically applying the electronic patient data to the risk variables in the outcome likelihood model, the baseline outcome likelihood model, and the dynamic outcome likelihood model as scoring functions;

aggregating patient histories for groups of patients similar to the actual patient;
determining whether at least one of the baseline outcome likelihood and dynamic outcome likelihood exceeds a predetermined threshold;
facilitating an intervention in treating the physiological adverse outcome type associated with the physiological condition of interest by including an attribution associated with at least one risk factor causing the predetermined threshold to be exceeded;
verifying an effectiveness of the intervention based on the aggregated patient histories for the groups of patients similar to the actual patient; and
outputting an electronic alert to a clinician if at least one of the baseline outcome likelihood and dynamic outcome likelihood exceeds the predetermined threshold to facilitate an intervention in treating the physiological condition associated with the adverse outcome type, the electronic alert including the intervention.

14. The process of claim 13 further comprising:
generating an alerting algorithm that compares computed values for at least one of the overall outcome likelihood, baseline outcome likelihood, and dynamic outcome likelihood against predetermined thresholds, where the alerting algorithm thresholds are based upon a balancing of true positive and false positive behavior; and
generating an attribution assessment for the adverse outcome type by:
evaluating the contribution of the selected risk variables with respect to at least one of the baseline outcome likelihood and the dynamic outcome likelihood associated with an occurrence of an adverse outcome; and
indicating at least one evaluated risk variable that is determined to be a key contributor to the overall outcome likelihood.

15. The process of claim 14, wherein:
evaluating the contributions of the selected risk variables comprises utilizing the computer for producing a vector of indices characterizing the strength of the contributions of individual risk variables to at least one of the baseline outcome likelihood and the dynamic outcome likelihood.

16. The process of claim 14 further comprising:
mapping actual patient data that is not represented in the training data set to the selected risk variables;
applying, by the computer, the mapped patient data in the selected risk variables to the outcome likelihood model, the baseline outcome likelihood model, and the dynamic outcome likelihood model, to compute the baseline outcome likelihood and dynamic outcome likelihood for the actual patient data; and
outputting a presentation of the results as predictions of the likelihoods of the adverse outcome for the patient represented by the actual patient data in response to results from the alerting algorithm.

17. The process of claim 13 further comprising identifying a set of candidate risk variables by:
identifying a specific physiological condition of interest associated with the adverse outcome type;
obtaining diagnostic information based upon the identified specific physiological condition;
obtaining information about clinical interventions that are likely to be appropriate interventions for the physiological condition of interest;
identifying other physiological conditions that are related to the physiological condition of interest;
populating a knowledgebase that is accessible by the computer, which relates the obtained diagnostic information to the physiological condition of interest and that relates the obtained clinical intervention information to the physiological condition of interest and that relates other identified physiological conditions to the physiological condition of interest; and
selecting the set of candidate risk variables using knowledge extracted from the populated knowledgebase.

18. The process of claim 17, wherein obtaining diagnostic information comprises:
identifying diagnostic criteria employed to diagnose the physiological condition of interest;
identifying corresponding risk metrics of the identified diagnostic criteria; and
identifying electronic sources for data fields necessary to employ the diagnostic criteria including electronic medical record data fields.

19. The process of claim 17 further comprising:
utilizing by the computer, an ontology of triple types allowed by the knowledgebase to identify queries to elicit the diagnostic information and clinical intervention information to build the knowledgebase.

20. The process of claim 13, wherein:
generating a dynamic outcome likelihood model form comprises at least one of:
defining an outcome likelihood model component corresponding to each selected risk variable in the dynamic group, and aggregating across comparisons of a component magnitude when calculated with the actual dynamic risk variable value to the component magnitude when calculated with an estimated value of the selected risk variable in the dynamic group that is produced by a corresponding one of the dynamic risk variable model forms; and
basing the dynamic outcome likelihood model form on a set of scores of selected risk variables in the dynamic group, one for each risk variable, where a score is calculated as the component magnitude of the corresponding outcome likelihood model component calculated with a known value of a risk variable in the dynamic group minus the component magnitude of the same outcome likelihood model component calculated with estimated values of the predictor variable produced by a dynamic risk variable model form; and
fitting the constructed outcome likelihood model form, baseline outcome likelihood model form, and dynamic outcome likelihood model form, to a training data set to produce a dynamic outcome likelihood model, comprises at least one of:
computing the dynamic outcome likelihood model form based on a set of dynamic risk variable scores, one for each risk variable, where a score is calculated as a magnitude of a corresponding outcome likelihood model component calculated with an actual dynamic risk variable value minus a magnitude of the same outcome likelihood model component calculated with estimated values of a predictor variable produced by a dynamic risk variable model form;
computing the dynamic outcome likelihood model form as the sum over a set of dynamic risk variable scores; and computing the dynamic outcome likelihood model form as the sum over a set of dynamic risk variable scores which are greater than zero.

* * * * *